US012679902B2

(12) United States Patent
Nakazawa et al.

(10) Patent No.: US 12,679,902 B2
(45) Date of Patent: Jul. 14, 2026

(54) METHOD FOR PRODUCING CELL POPULATION CONTAINING CAR-EXPRESSING IMMUNE CELLS

(71) Applicants: SHINSHU UNIVERSITY, Nagano (JP); KYOTO PREFECTURAL PUBLIC UNIVERSITY CORPORATION, Kyoto (JP); BrightPath Biotherapeutics Co., Ltd., Kanagawa (JP)

(72) Inventors: Yozo Nakazawa, Matsumoto (JP); Shigeki Yagyu, Kyoto (JP); Miyuki Tanaka, Matsumoto (JP); Kayoko Nakamura, Matsumoto (JP); Masahiro Okada, Sagamihara (JP); Makoto Kondo, Kawasaki (JP); Tomokuni Shigeura, Kawasaki (JP); Shogo Hirota, Tokyo (JP)

(73) Assignees: SHINSHU UNIVERSITY, Nagano (JP); KYOTO PREFECTURAL PUBLIC UNIVERSITY CORPORATION, Kyoto (JP); BRIGHTPATH BIOTHERAPEUTICS CO., LTD., Kanagawa (JP)

( * ) Notice: Subject to any disclaimer, the term of this patent is extended or adjusted under 35 U.S.C. 154(b) by 1151 days.

(21) Appl. No.: 17/626,345

(22) PCT Filed: Jul. 30, 2020

(86) PCT No.: PCT/JP2020/029308
§ 371 (c)(1),
(2) Date: Jan. 11, 2022

(87) PCT Pub. No.: WO2021/020526
PCT Pub. Date: Feb. 4, 2021

(65) Prior Publication Data
US 2022/0265714 A1      Aug. 25, 2022

(30) Foreign Application Priority Data
Jul. 31, 2019      (WO) .................. PCT/JP2019/029942

(51) Int. Cl.
| | |
|---|---|
| *A61K 35/17* | (2025.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 14/715* | (2006.01) |
| *C07K 16/32* | (2006.01) |
| *C12N 5/0783* | (2010.01) |
| *A61K 38/00* | (2006.01) |

(52) U.S. Cl.
CPC .............. *C07K 16/32* (2013.01); *A61K 40/11* (2025.01); *A61K 40/31* (2025.01); *A61K 40/4205* (2025.01); *A61K 40/4211* (2025.01); *A61K 40/422* (2025.01); *A61P 35/00* (2018.01); *C07K 14/70532* (2013.01); *C07K 14/70578* (2013.01); *C07K 14/715* (2013.01); *C12N 5/0636* (2013.01); *A61K 38/00* (2013.01); *C07K 2317/622* (2013.01); *C07K 2317/76* (2013.01); *C07K 2319/02* (2013.01); *C07K 2319/03* (2013.01); *C07K 2319/33* (2013.01); *C12N 2502/11* (2013.01); *C12N 2510/00* (2013.01)

(58) Field of Classification Search
CPC .... C07K 16/32; C07K 14/7051; A61K 40/11; A61K 40/31; A61K 40/4205; A61K 40/422; C12N 2510/00; C12N 5/0636; C12N 2502/11
See application file for complete search history.

(56) References Cited

U.S. PATENT DOCUMENTS

| | | |
|---|---|---|
| 8,822,647 B2 | 9/2014 | Jensen |
| 2013/0171152 A1 | 7/2013 | Spriggs et al. |
| 2016/0158285 A1 | 6/2016 | Cooper et al. |
| 2017/0333480 A1* | 11/2017 | Cooper .............. A61K 40/4211 |
| 2018/0244748 A1 | 8/2018 | Gill et al. |

(Continued)

FOREIGN PATENT DOCUMENTS

| | | |
|---|---|---|
| CN | 108025024 | 5/2018 |
| CN | 108251376 | 7/2018 |

(Continued)

OTHER PUBLICATIONS

Kershaw, M.H., Westwood, J.A. and Darcy, P.K., 2013. Gene-engineered T cells for cancer therapy. Nature Reviews Cancer, 13(8), pp. 525-541. (Year: 2013).*

(Continued)

*Primary Examiner* — Jeremy C Flinders
*Assistant Examiner* — Masudur Rahman
(74) *Attorney, Agent, or Firm* — Wenderoth, Lind & Ponack, L.L.P.

(57) ABSTRACT

The present disclosure includes a method of producing a cell population containing Chimeric Antigen Receptor (CAR)-expressing immune cells, comprising co-culturing CAR-expressing immune cells and cells expressing a target antigen of the CAR, wherein the CAR-expressing immune cells are cells into which a CAR gene has been introduced and the target antigen-expressing cells are normal blood cells that have been engineered to express the target antigen.

17 Claims, 7 Drawing Sheets
Specification includes a Sequence Listing.

(56) References Cited

U.S. PATENT DOCUMENTS

| | | | |
|---|---|---|---|
| 2018/0289742 A1 | 10/2018 | Nishio et al. | |
| 2018/0319862 A1 | 11/2018 | Thompson et al. | |
| 2019/0062426 A1 | 2/2019 | Kochenderfer | |
| 2019/0343880 A1 | 11/2019 | Hosoi | |

FOREIGN PATENT DOCUMENTS

| | | | | |
|---|---|---|---|---|
| JP | 2013-529061 | 7/2013 | | |
| JP | 2017-535284 | 11/2017 | | |
| JP | 2017-221211 | 12/2017 | | |
| JP | 2018-531014 | 10/2018 | | |
| JP | 2018-532432 | 11/2018 | | |
| WO | 2017/061615 | 4/2017 | | |
| WO | 2018/110374 | 6/2018 | | |
| WO | WO-2018110374 A1 * | 6/2018 | ............ | A61K 35/17 |
| WO | 2019/020089 | 1/2019 | | |
| WO | 2019/108932 | 6/2019 | | |

OTHER PUBLICATIONS

Noren, N.K., Foos, G., Hauser, C.A. and Pasquale, E.B., 2006. The EphB4 receptor suppresses breast cancer cell tumorigenicity through an Abl-Crk pathway. Nature cell biology, 8(8), pp. 815-825. (Year: 2006).*

Wilson, M.H., Coates, C.J. and George, A.L., 2007. PiggyBac transposon-mediated gene transfer in human cells. Molecular therapy, 15(1), pp. 139-145. (Year: 2007).*

Extended European Search Report issued Jul. 7, 2023 in corresponding European Patent Application No. 20847793.5, 10 pages.

Kebriaei et al., "Adoptive Therapy Using Sleeping Beauty Gene Transfer System and Artificial Antigen Presenting Cells to Manufacture T Cells Expressing CD19-Specific Chimeric Antigen Receptor", Blood, 2014, vol. 124, No. 21, pp. 1-3.

International Preliminary Report on Patentability mailed Feb. 10, 2022 in corresponding International (PCT) Patent Application No. PCT/JP2020/029308.

International Preliminary Report on Patentability mailed Feb. 10, 2022 in corresponding International (PCT) Patent Application No. PCT/JP2019/029942.

International Search Report issued Oct. 29, 2019 in corresponding International (PCT) Patent Application No. PCT/JP2019/029942.

International Search Report issued Oct. 6, 2020 in International (PCT) Application No. PCT/JP2020/29308.

Eshhar, Zelig et al., "Specific activation and targeting of cytotoxic lymphocytes through chimeric single chains consisting of antibody-binding domains and the γ and ζ subunits of the immunoglobulin and T-cell receptors", Proc. Natl. Acad. Sci., vol. 90, pp. 720-724, 1993.

Brentjens, Renier et al., "CD19-targeted T cells rapidly induce molecular remissions in adults with chemotherapy-refractory acute lymphoblastic leukemia", Sci Transl Med, vol. 5, No. 177, 19 pages, 2013.

Nakazawa, Yozo, "Gene-modified T-cell therapy using chimeric antigen receptor", Journal of Molecular Targeted Therapy for Cancer, vol. 13, No. 4, pp. 473-479, 2015.

Stock, S., et al., "Idelalisib for optimized CD 19-specific chimeric antigen receptor T cells in chronic lymphocytic leukemia patients", International Journal of Cancer, vol. 145, No. 5, 2019, pp. 1312-1324, XP093182100, US, ISSN: 0020-7136, DOI:10.1002/ijc.32201.

* cited by examiner

CMV promoter

HER2 cDNA

EF1α promoter co-stimulatory molecule cDNA*3

HER2
+
co-stimulatory molecule
double expression vector
(plasmid)

SV40 pA

*3: CD80, 4-1BBL, CD40, or OX40L (b)

CMV promoter

HER2 cDNA

EF1α promoter co-stimulatory molecule cDNA*4

HER2
+
co-stimulatory molecules
triple expression vector
(plasmid)

p2A sequence co-stimulatory molecule cDNA*5

SV40 pA

*4 : CD40
*5 : OX40L (c)

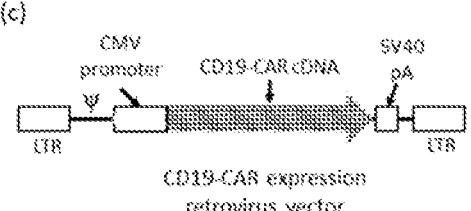

CMV promoter

CD19-CAR cDNA

SV40 pA

LTR

LTR

CD19-CAR expression
retrovirus vector

METHOD FOR PRODUCING CELL POPULATION CONTAINING CAR-EXPRESSING IMMUNE CELLS

TECHNICAL FIELD

The present disclosure relates to a cell population containing Chimeric Antigen Receptor (CAR)-expressing immune cells and a method of producing the same.

BACKGROUND

Treatment with Chimeric Antigen Receptor (CAR)-T cells, which are cytotoxic T cells (CTLs) whose T cell receptor (TCR) is genetically modified so that the CTLs directly and selectively recognize tumor cells to exert anti-tumor effects, has been developed as one of immunotherapies for cancer patients in recent years (Non-Patent Document 1) and attracting much attention as an extremely promising therapy for intractable tumors. The CAR is a general term for proteins that have, on its N-terminal side, a protein specifically recognizing a tumor antigen, such as a single-chain antibody (scFv) prepared by modifying antibody variable regions to a single-chain amino acid sequence, and, on its C-terminal side, the T cell receptor $\zeta$ chain. CAR-expressing T cells recognize the tumor antigen at the extracellular domain, transmit the signal into the T cells through the following $\zeta$ chain, and become activated to exert their antitumor effects by releasing cell killing factors such as perforin and granzyme (Non-Patent Document 1).

Cancer treatments using CAR-T cells have already been approved and put into practical use in Japan, Europe and the United States for some tumors. In the area of blood tumors, a phase III clinical trial was conducted for CD19-positive B lymphocytic tumor, wherein a CD19-specific CAR was introduced into T cells collected in advance from patients with recurrent acute lymphocytic leukemia by gene transfer, and the cells were cultured, expanded and infused into the patients' bodies. Then, it was reported that molecular biological remission in bone marrow was obtained in all 5 patients who received the administration (Non-Patent Document 2). Based on this report, two drugs, Tisagen lecleucel (product name: Kymriah®) and Axicabtagene ciloleucel (product name: Yescarta®), have been approved for CD19-positive acute lymphocytic leukemia and lymphoma and put on the market in Europe and the United States. They have attracted a great deal of attention as a breakthrough treatment for intractable CD19-positive lymphocytic leukemia and lymphoma, which have been difficult to cure to date.

Most of the clinically applied CAR-T cell preparations have been produced by gene modification using γ-retrovirus. Cell preparations produced by virus-mediated gene modification are manufactured through extremely complicated processes including GMP grade virus production, residue testing of the final product for viruses, and production in accordance with Cartagena Approval of Type 1 Use in some countries.

For producing CAR-T cells, in addition to the conventional methods using viral vectors, gene modification techniques using non-viral vectors have also been used (Patent Documents 1 and 2). For example, focusing on a gene transfer technology that does not use γ-retrovirus but utilizes a transposon called piggyBac (hereinafter referred to as "piggyBac transposon-mediated method"), research and development of non-virally genetically modified CAR-T cell therapies are also being carried out. CAR-T cell production by the non-viral gene modification technology is a safe and simple method for CAR-T cell production because no virus is used for gene transfer. The ACE method, a culturing method for non-virally genetically modified CAR-T cells that has been developed by one of the inventors Nakazawa et al. (Patent Document 2), is a pioneer method for non-viral gene modification and has overcome the issues of the production methods using viral vectors.

PRIOR ART DOCUMENTS

Patent Documents

Patent document 1: JP2017-22121A
Patent document 2: WO2017/061615

Non-Patent Documents

Non-Patent Document 1: Eshhar Z, Waks T, Gross G, Schindler D G., Specific activation and targeting of cytotoxic lymphocytes through chimeric single chains consisting of antibody-binding domains and the gamma or zeta subunits of the immunoglobulin and T-cell receptors. Proc Natl Acad Sci USA. 1993; 90:720-724.

Non-Patent Document 2: Brentjens R J, Davila M L, Riviere I, Park J, Wang X, Cowell L G, Bartido S, Stefanski J, Taylor C, Olszewska M, Borquez-Ojeda O, Qu J, Wasielewska T, He Q, Bernal Y, Rijo I V, Hedvat C, Kobos R, Curran K, Steinherz P, Jurcic J, Rosenblat T, Maslak P, Frattini M, Sadelain M. CD19-targeted T cells rapidly induce molecular remissions in adults with chemotherapy-refractory acute lymphoblastic leukemia. Sci Transl Med. 2013; 5:177ra38.

SUMMARY

Problem to be Solved

Conventional methods for producing CAR-T cells can obtain CAR-T cells at a clinically available quality and number for target molecules of blood tumors such as CD19. It has been difficult, however, to obtain a sufficient number of cells for clinical use for target molecules of solid tumors. Also, attempts to secure the number of cells required for administration to patients by long-term culture or forced activation by co-stimulatory molecules can change the characteristics of T cells so that the T cells have less cytotoxic activity and are easily exhausted. Thus, it has been difficult to stably produce CAR-T cells of sufficient number and quality for clinical application.

Means to Solve Problem

The present inventors have diligently studied to solve the above problems. Then, the inventors have found that co-culturing CAR-introduced immune cells such as CAR-T cells with separately prepared target antigen-expressing cells that express the target antigen of the CAR not only improves gene transfer efficiency and cell proliferation rate but also enables stable culturing of immune cells that have high cytotoxic activity and are not easily exhausted.

That is, the present disclosure, in an aspect, provides a method of producing a cell population containing Chimeric Antigen Receptor (CAR) -expressing immune cells, comprising co-culturing CAR-expressing immune cells and cells expressing a target antigen of the CAR, wherein the CAR-expressing immune cells are cells into which a CAR gene has been introduced and the target antigen-expressing cells are normal blood cells that have been engineered to express the target antigen.

The present disclosure, in a further aspect, provides a cell population containing Chimeric Antigen Receptor (CAR)-expressing immune cells produced by the method as defined above.

The present disclosure, in a further aspect, provides a composition for treating cancer comprising the cell population as defined above.

Effect of Invention

According to the present invention, the production efficiency of CAR-expressing immune cells can be increased and CAR-T cells having high cytotoxic activity can be stably produced. In particular, the production efficiency of CAR-expressing immune cells for solid tumors can be dramatically improved, and thus CAR-T cell therapies can be applied to various cancer types.

BRIEF DESCRIPTION OF DRAWINGS

FIG. 3 shows the target antigen expression vector used in the example section.

FIG. 6 shows the results of the killing assay (first) targeting HER-expressing U2OS cells with HER2-CAR-expressing T cells.

FIG. 7 shows the results of the killing assay (second) targeting HER-expressing U2OS cells with HER2-CAR-expressing T cells.

DETAILED DESCRIPTION OF EMBODIMENTS

Figure 1:
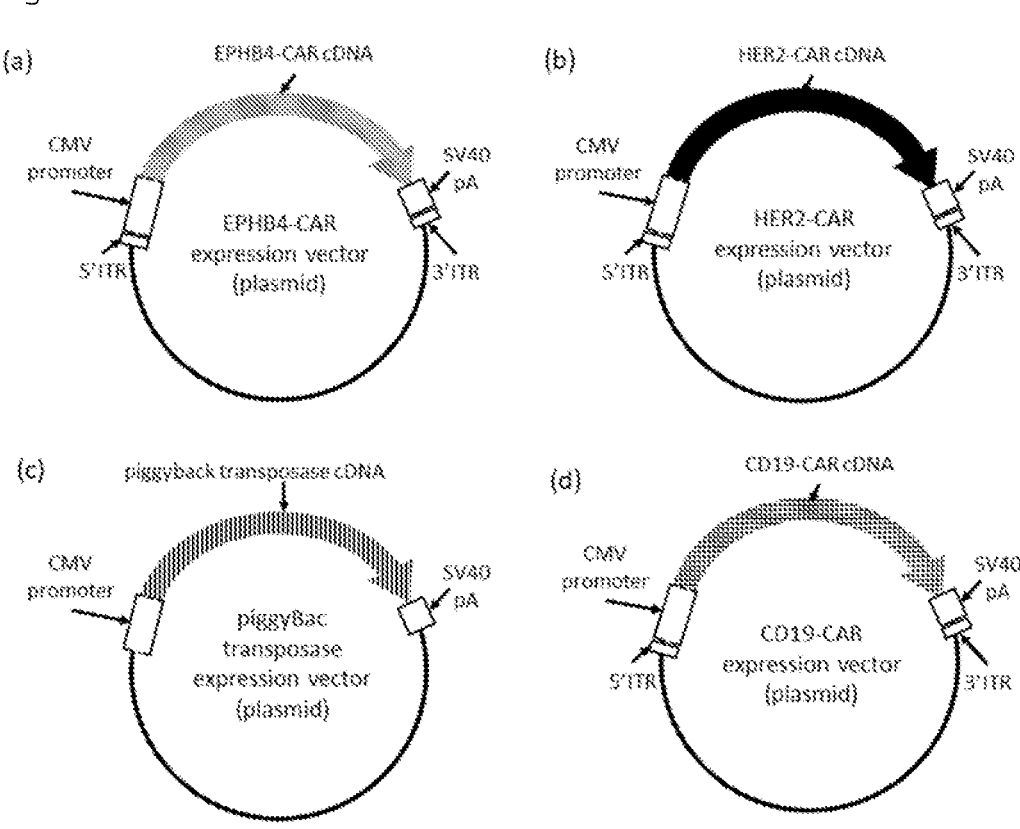
FIG. 1 shows the CAR gene expression vector and the transposase expression vector used in the example section.

Unless otherwise specified, the terms used in this disclosure have meanings commonly understood by those skilled in the art in the fields such as organic chemistry, medical science, pharmaceutical science, molecular biology, and microbiology. The followings are definitions of some terms used in this disclosure and these definitions supersede the common understandings in this disclosure.

In the present disclosure, when a number is accompanied by the term "about", it is intended to include a range of ±10% of that value. For example, "about 20" shall include "18 to 22". A range of numbers includes all numbers between the endpoints and the numbers at the endpoints. The term "about" used for a range applies to both ends of the range. Thus, for example, "about 20 to 30" shall include "18 to 33".

In the present disclosure, sequence identity means the degree of sequence matching between polypeptides or polynucleotides, and it is determined by comparing two sequences optimally aligned (aligned such that the amino acid or nucleotide matching is maximized) over the region of the sequence to be compared. The number of sequence identity (%) is calculated by determining the same amino acids or nucleotides present in both sequences, determining the number of matching sites, dividing the number of matching sites by the total number of amino acids or nucleotides in the sequence region to be compared, and then multiplying the obtained value by 100. Examples of algorithms for obtaining the optimal alignment and sequence identity include various algorithms commonly available to those skilled in the art (e.g., BLAST algorithm, FASTA algorithm). The sequence identity can be determined, for example, by using a sequence analysis software such as BLAST or FASTA.

Chimeric Antigen Receptor

A chimeric antigen receptor (herein also referred to as CAR) is a protein having a structure containing a target-specific extracellular domain, a transmembrane domain, and an intracellular signal domain that works for the effector function of immune cells from the N-terminal side to the C-terminal side of the protein. A CAR gene is a gene encoding this receptor. Each domain will be described hereinafter.

(a) Extracellular Domain

The extracellular domain contains an antigen recognition site that exhibits target-specific binding. For example, the extracellular domain may contain a scFv fragment of a monoclonal antibody against the target (e.g., the fragment consisting of the amino acid sequence of SEQ ID NO: 1 or 2, or described in WO2017/061615, CN107164338A, WO2016/123143, WO2016/023253, or JP2018-198601A), or, when the target is a receptor, a ligand that binds to the receptor (e.g., a ligand consisting of the amino acid sequence of SEQ ID NO: 3, or described in WO2018/110374 or WO2018/052142). The monoclonal antibody as used herein can be, for example, a rodent (such as mouse, rat, or rabbit) antibody, a human antibody, or a humanized antibody. The humanized monoclonal antibody is an antibody prepared by making the structure of a monoclonal antibody of a non-human animal (e.g., mouse or rat) resemble to that of a human antibody, and includes a humanized chimeric antibody in which only the constant region of an antibody is replaced with that of a human antibody, and a humanized CDR-grafted antibody in which the constant region and the portions other than the Complementary Determination Regions (CDRs) in the variable region are replaced with those of a human antibody (P. T. Johns et al., Nature 321, 522, 1986). In order to enhance the antigen-binding activity of a humanized CDR-grafted antibody, improved techniques have already been developed and can be used to make humanized antibodies and they include, for example, selection of framework (FR) regions of a human antibody with high homology with those of a mouse antibody, production of a humanized antibody with high homology with a mouse antibody, and substitution of amino acids in the FR regions after transplant of mouse CDRs to a human antibody (see, for example, U.S. Pat. Nos. 5,585,089B, 5,693,761B, 5,693,762B, 6,180,370B, EP451216B, EP682040B, JP2828340B).

The scFv fragment has a structure in which a light chain variable region (VL) and a heavy chain variable region (VH) of an immunoglobulin are connected via a linker, and it retains the ability to bind to an antigen. As the linker, for example, a peptide linker can be used. A peptide linker is a linker being a peptide, in which amino acids are linearly connected. Examples of peptide linkers include linkers composed of glycine and/or serine (e.g., GGS or GS linker). Glycine and serine are small in size, preventing the linker from forming a higher-order structure. The length of the linker is not particularly limited to any specific length. For example, a linker having 5 to 25 amino acid residues can be used. The length of the linker is preferably 8 to 25, more preferably 15 to 20.

The target antigen can be an antigen that is significantly or markedly expressed in tumor cells as compared to non-tumor cells. Examples of target antigens include, for example, tumor-related or tumor-specific antigens, such as EPHB4, HER2, EPHA2, EPHB2, EGFR, GD2, Glypican-3, 5T4, 8H9, αvβ6 integrin, B cell maturation antigen (BCMA), B7-H3, B7-H6, CAIX, CA9, CD19, CD20, CD22, κ light chain, CD30, CD33, CD38, CD44, CD44v6, CD44v7/8, CD70, CD116, CD123, CD138, CD171, CEA, CSPG4, EGFR, EGFRvIII, EGP2, EGP40, EPCAM, ERBB3, ERBB4, FAP, FAR, FBP, fetal AchR, folic acid receptor oa, GD3, HLA-AI MAGE A1, HLA-A2, IL11Ra, IL13Ra2, KDR, Lambda, Lewis Y, MCSP, mesothelin, MUC1, MUC4, MUC6, NCAM, NKG2D ligand, NY-ESO-1, PRAME, PSCA, PSC1, PSMA, ROR1, Sp17, SUR-VIVIN, TAG72, TEM1, TEM8, VEGF receptor 2, carcinoembryonic antigen, HMW-MAA, VEGF receptor, fibronectin, tenascin, or antigens present in the extracellular matrix such as carcinoembryonic antigen (CEA) in the necrotic regions of tumors, or proteins containing mutations identified by genomic analysis and/or differential expression studies of tumors.

When the target antigen is a receptor, a ligand for the receptor can be used as an antigen recognition site instead of scFv. For example, the extracellular domain of EFNB2 protein, which is a natural ligand for EPHB4 receptor, and GM-CSF, which is a ligand for GM-CSF receptor, as well as Adnectin for EGFR, IL-11 for IL11Ra, IL-13 for IL13Ra2, and FSH for FSHR, T1E for the ERBB2 family, CD27 for CD70, DNAM-1 for Nectin-2, NKG2D for MICA and MICB, and NKp30 for Gal3 can be used.

The production method of the present disclosure can obtain CAR-expressing immune cells in a sufficient number and quality not only for antigens expressed in blood cells but also for those not expressed in such cells, and it is particularly suitable for target antigens for solid tumors. Examples of such target antigens include EPHB4, HER2, EPHA2, EPHB2, EGFR, GD2, Glypican-3, 5T4, MUC1, MUC4, MUC6, NCAM, EGFR, EGFRvIII, ERBB3, ERBB4, NY-ESO-1, PSCA, PSC1, PSMA, VEGFR receptor 2, carcinoembryonic antigen, HMW-MAA, and VEGF receptor.

The extracellular domain may contain a leader sequence (signal peptide) that facilitates translocation of CAR to the cell surface. As the leader sequence, for example, the leader sequence of GM-CSF receptor can be used.

In an embodiment, the extracellular domain comprises or consists of an amino acid sequence having 90% or more sequence identity with the amino acid sequence of any one of SEQ ID NOs: 1 to 3, preferably the amino acid sequence of SEQ ID NO: 1. In a further embodiment, the extracellular domain comprises or consists of the amino acid sequence of any one of SEQ ID NOs: 1 to 3, preferably the amino acid sequence of SEQ ID NO: 1.

(b) Transmembrane Domain

The transmembrane domain lies between the extracellular domain and the intracellular signal domain. As the transmembrane domain, a transmembrane domain of CD8, T cell receptor α or β chain, CD28, CD3E, CD45, CD4, CD5, CD8, CD9, CD16, CD22, CD33, CD37, CD64, CD80, CD86, CD134, CD137, CD154, GITR, or 4-1BB can be used. The transmembrane domain can also be an artificially constructed polypeptide. Preferably, the transmembrane domain is the transmembrane domain of CD28 (e.g., the domain consisting of the amino acid sequence of SEQ ID NO: 7 or 8).

In an embodiment, the transmembrane domain comprises or consists of an amino acid sequence having 90% or more sequence identity with the amino acid sequence of SEQ ID NO: 7 or 8. In a further embodiment, the transmembrane domain comprises or consists of the amino acid sequence of SEQ ID NO: 7 or 8.

(c) Intracellular Signal Domain

The intracellular signal domain transmits a signal necessary for immune cells to exert its effector function. That is, the intracellular signal domain to be used is capable of transmitting a signal necessary for activating the immune cells when the extracellular domain binds to the target antigen. The intracellular signal domain comprises a domain for transmitting a signal mediated by TCR complex (referred to as "first domain" for convenience), and may further comprise a domain for transmitting a co-stimulatory signal (referred to as "second domain" for convenience). Examples of these domains include domains of CD2, CD4, CD5, CD28, CD134, 4-1BB (CD137), GITR, CD27, OX40, HVEM, CD3ζ, FcεRIγ, OX-40, and ICOS. The first domain is preferably the domain of CD3ζ or FcεRIγ, more preferably the domain of CD3ζ (e.g., the domain consisting of the amino acid sequence of SEQ ID NO: 9). The second domain is preferably the domain of CD28, 4-1BB (CD137), CD2, CD4, CD5, CD134, OX-40 or ICOS, and more preferably the domain of CD28 or 4-1BB. The first domain and the second domain may each be composed of a plurality of the same or different domains connected in tandem.

When the intracellular signal domain includes the first domain and the second domain, the first domain and the second domain may be connected in any way, but the second domain is preferably placed on the transmembrane domain side, since it is known that the co-stimulation was strongly transmitted in some cases when the CD3ζ was connected distally. The first domain and the second domain may be directly connected or may be connected by a linker. As the linker, for example, a peptide linker can be used. The peptide linker is a linker being a peptide, in which amino acids are linearly connected, and its structure and characteristics are described above. The linker that connects the first domain and the second domain may be a linker composed of glycine only. The length of the linker is not particularly limited to any specific length. For example, a linker having 2 to 15 amino acid residues can be used.

In an embodiment, the intracellular signal domain comprises or consists of an amino acid sequence having 90% or more sequence identity with the amino acid sequence of SEQ ID NO: 9. In a further embodiment, the extracellular domain comprises or consists of the amino acid sequence of SEQ ID NO: 9.

(d) Other Elements

The extracellular domain and the transmembrane domain may be connected via a spacer domain. The spacer domain is used to promote the binding of the CAR to the target antigen. As the spacer domain, an Fc fragment of an antibody or a fragment or derivative thereof, a hinge region of an antibody or a fragment or derivative thereof, a CH2 region of an antibody, a CH3 region of an antibody, an artificial spacer sequence, or a combination thereof (e.g., the domain consisting of the amino acid sequence of any one of SEQ ID NOs: 4-6) can be used. For example, an Fc fragment of human IgG (e.g., human IgG1, human IgG4) can be used as the spacer domain. In addition, a part of the extracellular domain of CD28 and a part of the extracellular domain of CD8a can also be used as the spacer domain. A spacer domain can also be provided between the transmembrane domain and the intracellular signal domain.

In an embodiment, the spacer domain comprises or consists of an amino acid sequence having 90% or more sequence identity with the amino acid sequence of any one of SEQ ID NOs: 4-6. In a further embodiment, the spacer domain comprises or consists of the amino acid sequence of any one of SEQ ID NOs: 4-6.

CAR Expression Vector

In the present disclosure, CAR-expressing immune cells are prepared by introducing a CAR gene into immune cells using a CAR expression vector. The CAR expression vector means a nucleic acid molecule capable of transporting a nucleic acid molecule encoding a CAR gene into immune cells. It can be DNA or RNA in any form and of any origin, and various types of vectors are available. The vector can be a viral vector or a non-viral vector. Examples of viral vectors include retrovirus vectors, lentivirus vectors, adenovirus vectors, adeno-associated virus vectors, herpesvirus vectors, and Sendai virus vectors. Among these, with a retrovirus vector, a lentivirus vector, and an adeno-associated virus vector, the gene of interest incorporated into the vector is integrated into the host chromosome and stable and long-term expression is expected. Each viral vector can be prepared according to conventional methods or by using commercially available kits for this purpose. Examples of non-viral vectors include plasmid vectors, liposome vectors, and positively charged liposome vectors (Felgner, P. L., Gadek, T. R., Holm, M. et al., Proc. Natl. Acad. Sci., 84: 7413-7417, 1987), YAC vectors, and BAC vectors.

The CAR expression vector comprises an expression unit for expressing a CAR gene, which usually comprises a promoter, a CAR gene, and a poly A addition signal. Examples of promoters that can be used in the CAR expression cassette include CMV-IE (cytomegalovirus early gene-derived promoter), SV40ori, retrovirus LTRSRα, EF1α, and β-actin promoter. Examples of poly A addition signal sequences include a poly A addition sequence of SV40, a poly A addition sequence of a bovine growth hormone gene, and a poly A addition sequence of globulin. The CAR gene is usually connected to the 3'end of the promoter directly or via another sequence so that the promoter regulates expression of the CAR gene, and the poly A addition signal sequence is placed downstream of the CAR gene. The CAR gene is transcribed into messenger RNA (mRNA) from such an expression unit, and the CAR is translated from the mRNA and presented on the cell surface.

The expression unit may comprise a gene for detection of gene expression (e.g., reporter gene, cell or tissue-specific gene, or selectable marker gene), an enhancer sequence for improving expression efficiency, a WRPE sequence, for example.

The gene for detection is used for determining success or failure and efficiency of introduction of the CAR expression vector, detecting expression or determining expression efficiency of the CAR gene, or selecting or sorting cells expressing the CAR gene. Examples of genes for detection include neo gene that confers resistance to neomycin, npt gene (Herrera Estrella, EMBO J. 2 (1983), 987-995) and nptII gene (Messing & Vierra, Gene 1 9:259-268 (1982)) that confer resistance to kanamycin or other antibiotics, hph gene that confers resistance to hygromycin (Blochinger and Diggl mann, Mol Cell Bio 4: 2929-2931), and dhfr gene that confers resistance to methotrexate (Bourouis et al., EMBO J.2 (7)) (examples of marker genes); luciferase gene (Giacomin, P1. Sci. 116(1996), 59-72; Scikantha, J. Bact. 178 (1996), 121), β-glucuronidase (GUS) gene, genes for fluorescent proteins such as GFP (Gerdes, FEBS Lett. 389 (1996), 44-47) or variants thereof (e.g., EGFP, d2EGFP) (examples of reporter genes); and epidermal growth factor receptor (EGFR) gene lacking the intracellular domain. The gene for detection may be connected to the CAR gene via, for example, a bicistronic control sequence (e.g., ribosome internal recognition sequence (IRES)) or a sequence encoding a self-cleaving peptide. Examples of self-cleaving peptides include 2A peptide derived from Thosea asigna virus (T2A). Different examples of self-cleaving peptides include picornavirus-derived 2A peptide (F2A), foot-and-mouth disease virus (FMDV)-derived 2A peptide (F2A), equine rhinitis A virus (ERAV)-derived 2A peptide (E2A), and porcine teschovirus (PTV-1)-derived 2A peptide (P2A), and rotavirus, insect virus, aft virus or tripanosoma virus-derived 2A peptide, but are not limited thereto.

Immune Cells

In the present disclosure, the CAR gene is introduced into immune cells. The immune cells in the present disclosure may be T cells (including CD4-positive CD8-negative T cells, CD4-negative CD8-positive T cells, αβ-T cells, γδ-T cells, and NKT cells), B cells, NK cells, monocytes, macrophages, dendritic cells or combinations thereof. The immune cells may be cells isolated from humans or may be cells differentiated from cells such as iPS cells, ES cells, or hematopoietic stem cells. Also, the immune cells may be either autologous cells or allogeneic cells. In the present disclosure, the term "autologous cells" means cells obtained from a subject to which a cell population produced by the method of the present disclosure is to be administered, or cells derived from such obtained cells. The term "allogeneic cells" means that the cells are not the "autologous cells". Preferably, the immune cells are autologous cells. In an embodiment, the immune cells are lymphocytes (i.e., T cells, B cells, NK cells, or a combination thereof). In a further embodiment, the immune cells are T cells. CAR-expressing immune cells can be obtained by gene transfer into a cell population containing immune cells or progenitor cells thereof such as hematopoietic stem cells. For example, CAR-expressing immune cells may be obtained by differentiation of cells such as iPS cells, ES cells, or hematopoietic stem cells into which a CAR gene have been introduced, or may be obtained by differentiation of cells that have been transformed into iPS cells after a CAR gene have been introduced. In an embodiment, the CAR-expressing immune cells are prepared by introduction of a CAR gene into blood cells. In the present disclosure, the term "blood cell" or "blood cells" means a cell or cells constituting blood, and is used to mean a single cell or a cell population containing a plurality of cells, and in the sense of a cell population composed of one type of cells and also in the sense of a cell population containing multiple types of cells. Blood cells are preferably blood cells other than erythrocytes and platelets, and such blood cells include immune cells such as lymphocytes and monocytes. The blood cells may be cells isolated from humans or cells differentiated from cells such as iPS cells, ES cells, or hematopoietic stem cells, and may be either autologous cells or allogeneic cells, but preferably autologous cells. In a further embodiment, the CAR-expressing immune cells are prepared by introduction of a CAR gene into PBMCs. The PBMCs are preferably autologous PBMCs (i.e., PBMCs collected from a subject to which a cell population produced by the method of the present disclosure is to be administered). PBMCs can be prepared by conventional methods, for example, by referring to Saha S, Nakazawa Y, Huye L E, Doherty J E, Galvan D L, Rooney C M, Wilson M H. J Vis Exp. 2012 Nov. 5; (69): e4235. Unless otherwise specified, any cells herein described (e.g., T cells) are human cells.

Preparation of CAR-Expressing Immune Cells

The CAR gene expression vector prepared for gene transfer is introduced into immune cells by conventional methods. In the case of a viral vector, it is introduced into cells by viral infection. In the case of a non-viral vector such as a plasmid, conventional methods such as methods mediated by electroporation, liposome, or calcium phosphate can be used for introduction into cells, and the introduction is preferably carried out by electroporation.

In order to improve efficiency of integration into the host chromosome, it is preferable to carry out the gene transfer by a method mediated by transposon. The transposon-mediated method is one of non-viral gene transfer methods, and it can integrate a gene of interest into the host chromosome by utilizing the mechanism by which an enzyme acting on the genome (transposase) and its specific recognition sequence cause gene translocation in combination. The transposon-mediated method can be, for example, the piggyBac transposon-mediated method. The piggyBac transposon-mediated method utilizes a transposon isolated from an insect (Fraser M J et al., Insect Mol Biol. 1996 May; 5(2):141-51.; Wilson M H et al., Mol THER2007 January; 15(1):139-45.) and it enables highly efficient integration into mammalian chromosomes. The piggyBac transposon-mediated method is practically used for gene transfer already (see, for example, Nakazawa Y, et al., J Immunother 32:826-836, 2009; Nakazawa Y et al., J Immunother 6:3-10, 2013).

The transposon-mediated method is not limited to the one using piggyBac, and can use a transposon such as Sleeping Beauty (Ivics Z, Hackett P B, Plasterk R H, Izsvak Z (1997) Cell 91: 501-510.), Frog Prince (Miskey C, Izsvak Z, Plasterk R H, Ivics Z (2003) Nucleic Acids Res 31: 6873-6881.), Tol1 (Koga A, Inagaki H, Bessho Y, Hori H. Mol Gen Genet. 1995 Dec. 10; 249(4):400-5.; Koga A, Shimada A, Kuroki T, Hori H, Kusumi J, Kyono-Hamaguchi Y, Hamaguchi S. J Hum Genet. 2007; 52(7):628-35. Epub 2007 Jun. 7.), Tol2 (Koga A, Hori H, Sakaizumi M (2002) Mar Biotechnol 4: 6-11.; Johnson Hamlet M R, Yergeau D A, Kuliyev E, Takeda M, Taira M, Kawakami K, Mead P E (2006) Genesis 44: 438-445.; Choo B G, Kondrichin I, Parinov S, Emelyanov A, Go W, Toh W C, Korzh V (2006) BMC Dev Biol 6: 5.).

The process of gene transfer by the transposon-mediated method can be a conventional process. For example, the piggyBac transposon-mediated method can be carried out by preparing a vector carrying a gene encoding the piggyBac transposase (a transposase plasmid) and a vector having a structure in which a CAR gene expression unit is sandwiched between piggyBac reverse repeat sequences (a transposon plasmid) and introducing these vectors into target cells by any of various methods such as electroporation, nucleofection, lipofection, and calcium phosphate-mediated method.

Preparation of Target Antigen-Expressing Cells

In the present disclosure, in addition to the CAR-expressing immune cells, normal blood cells engineered to express a target antigen are used as target antigen-expressing cells. The target antigen-expressing cells are cells that have been engineered to express a part or all of a target antigen on the cell surface so that the CAR introduced into CAR-expressing immune cells can bind to the target antigen. The target antigen in the present disclosure means a target antigen recognized by a CAR, and may be a protein, a sugar chain, or a glycolipid expressed on the cell surface so that the CAR introduced into immune cells can bind to it. Examples of target antigens include, for example, tumor-related or tumor-specific antigens targeted by the aforementioned CAR, such as EPHA2, HER2, EPHB2, EPHB4, EGFR, GD2, Glypican-3, HER2, 5T4, 8H9, avβ6 integrin, B cell maturation antigen (BCMA), B7-H3, B7-H6, CAIX, CA9, CD19, CD20, CD22, κ light chain, CD30, CD33, CD38, CD44, CD44v6, CD44v7/8, CD70, CD116, CD123, CD138, CD171, CEA, CSPG4, EGFR, EGFRvIII, EGP2, EGP40, EPCAM, ERBB3, ERBB4, ErbB3/4, FAP, FAR, FBP, fetal AchR, folic acid receptor α, GD2, GD3, HLA-AI MAGE A1, HLA-A2, IL11Ra, IL13Ra2, KDR, Lambda, Lewis Y, MCSP, mesothelin, MUC1, MUC4, MUC6, NCAM, NKG2D ligand, NY-ESO-1, PRAME, PSCA, PSC1, PSMA, ROR1, Sp17, SURVIVIN, TAG72, TEM1, TEM8, VEGF receptor 2, carcinoembryonic antigen, HMW-MAA, VEGF receptor, fibronectin, tenascin, or antigens present in the extracellular matrix such as carcinoembryonic antigen (CEA) in the necrotic regions of tumors, or proteins containing mutations identified by genomic analysis and/or differential expression studies of tumors.

In an embodiment, the target antigen comprises or consists of an amino acid sequence having 90% or more sequence identity with the amino acid sequence of SEQ ID NO: 10, 11, or 16, preferably the amino acid sequence of SEQ ID NO: 10. In a further embodiment, the target antigen comprises or consists of the amino acid sequence of SEQ ID NO: 10, 11, or 16, preferably the amino acid sequence of SEQ ID NO: 10.

The target antigen-expressing cells can be prepared, to express the target antigen, by introducing a gene encoding the target antigen into cells using a vector having an expression unit for expressing the target antigen gene, as described for the CAR-expressing immune cells. Alternatively, the target antigen-expressing cells can also be prepared by preparing mRNA of the target antigen gene and introducing the mRNA directly into cells. In addition, the target antigen-expressing cells can be prepared, to express the target antigen, by introducing another gene that induces expression of the target antigen into cells instead of the gene encoding the target antigen, or treating cells with an agent that induces expression of the target antigen, such as a low molecular weight compound, growth factor, hormone or cytokine. For example, treatment with sialic acid or a histone deacetylase inhibitor can prepare target antigen-expressing cells that express GD2. In an embodiment, the target antigen-expressing cells are prepared by introducing a target antigen gene into cells, and thus, the target antigen-expressing cells comprise an exogenous target antigen gene.

The target antigen-expressing cells may be prepared by introducing a co-stimulatory molecule gene together with a target antigen gene into cells to express the target antigen and the co-stimulatory molecule on the cell surface. That is, in an embodiment, the target antigen-expressing cells comprise one or more genes for one or more exogenous co-stimulatory molecules. Examples of co-stimulatory molecules include CD40, CD80, 4-1BB ligand (4-1BBL), OX40, OX40L, CD52, CD54, CD70, CD58, CD86, CD95, CD252, CD275, and a ligand for the integrin family (e.g., CD49a to CD49h, CD51, CD103, CD41, CDlla to 11c, ITGA9 to 11, CD18, CD19, CD61, ITGB4 to 8). In an embodiment, the co-stimulatory molecule is at least one co-stimulatory molecule selected from CD40, CD80, 4-1BBL, OX40L, preferably CD80 and/or 4-1BBL, more preferably CD80 and 4-1BBL.

In an embodiment, the co-stimulatory molecule comprises or consists of an amino acid sequence having 90% or more sequence identity with the amino acid sequence of any one of SEQ ID NOs: 12 to 15. In a further embodiment, the co-stimulatory molecule comprises or consists of the amino acid sequence of any one of SEQ ID NOs: 12-15.

The co-stimulatory molecule gene can be introduced by gene transfer using an expression vector comprising the co-stimulatory molecule gene and the target antigen gene; or by gene transfer introducing an expression vector or mRNA of the co-stimulatory molecule and that of the target antigen simultaneously or separately, wherein the expression vector or mRNA of the co-stimulatory molecule is separate from that of the target antigen.

The cells to be processed to express the target antigen gene to prepare the target antigen-expressing cells are normal blood cells (that is, blood cells excluding cancerous cells or a cell line derived therefrom) and not particularly limited to, but can be, cells isolated from humans, cells differentiated from cells such as iPS cells, ES cells, or hematopoietic stem cells, and may be either autologous cells or allogeneic cells, but preferably autologous cells. The blood cells are preferably blood cells other than erythrocytes and platelets, and such blood cells include immune cells such as lymphocytes and monocytes. The target antigen-expressing cells can be immune cells such as lymphocytes to which a target antigen gene have been introduced, or cells in which expression of the target antigen has been induced by introduction of another gene or by treatment with an agent. The target antigen-expressing cells may also be cells obtained by introducing a target antigen gene or another gene that induces expression of the target antigen into progenitor cells such as iPS cells, ES cells, or hematopoietic stem cells, and then differentiating the cells. In a preferred embodiment, the target antigen-expressing cells are prepared from PBMCs, preferably by gene transfer into PBMCs. In an embodiment, the target antigen-expressing cells are prepared by introduction of a target antigen gene into PBMCs. When PBMCs are used, CAR-expressing immune cells with high proliferation efficiency and high quality can be obtained. In addition, when PBMCs are used, it is possible to efficiently produce CAR-expressing immune cells without introducing a co-stimulatory molecule gene. The PBMCs are preferably autologous PBMCs (i.e., PBMCs taken from a subject to which a cell population produced by the method of the present disclosure is to be administered). When the autologous PBMCs are used, it is not necessary to remove the target antigen-expressing cells to prepare cells to be administered to a patient. Further, the target antigen-expressing cells and the CAR-expressing immune cells are both preferably prepared from PBMCs of the same subject, and more preferably from autologous PBMCs.

In the gene transfer into target antigen-expressing cells, the gene expression may be either transient or constitutive. Since appropriate and transient stimulation of the CAR and the co-stimulatory molecule on the surface of CAR-expressing immune cells is sufficient, and for the purpose of obtaining a cell population with a high proportion of CAR-expressing immune cells in a relatively short period of time, the gene transfer is preferred to use a target antigen gene expression vector intended for transient gene expression.

In order to obtain a cell population with a high proportion of CAR-expressing immune cells, it is preferable that target antigen-expressing cells are treated to lose its proliferative ability before co-cultured with CAR-expressing immune cells. The treatment that causes loss of proliferative ability is typically irradiation of radiation or ultraviolet, but may be treatment with an agent. The radiation irradiation is performed, for example, by irradiating gamma ray with an intensity of 25 Gy to 50 Gy for 15 to 30 minutes. The ultraviolet irradiation is performed, for example, by setting the dose to 2 to 400 mJ/cm², preferably 6 to 200 mJ/cm². By such treatments, proliferation of CAR-expressing immune cells become dominant, and a sufficient number and quality of cells for clinical application can be obtained.

Co-Culture

By co-culturing CAR-expressing immune cells and target antigen-expressing cells, the CAR-expressing immune cells proliferate efficiently by antigen stimulation from the target antigen-expressing cells.

The CAR-expressing immune cells are preferably cells that have been cultured after introduction of the CAR gene for, for example, about 8 hours to 2 weeks, considering recovery of the cells and stable expression of the transgene. Since the CAR-expressing immune cells can be exhausted by long-term culture, the cells are used for co-culture more preferably within 8 hours to 1 week, 8 hours to 72 hours, or 24 hours to 72 hours after the CAR gene transfer. The target antigen-expressing cells should sufficiently express the target antigen by the start of co-culture after the process for expressing the target antigen, such as gene transfer into the cells or treatment of the cells with an agent. For example, it is preferable that the target antigen-expressing cells have undergone the process for expressing the target antigen 8 or more hours before the start of co-culture.

The method of the present disclosure may comprise preparing CAR-expressing immune cells and/or target antigen-expressing cells prior to the co-culture. For example, the method of the present disclosure may comprise introducing a CAR gene into immune cells and/or carrying out a process for expressing a target antigen of the CAR on normal blood cells. The method of the present disclosure may further comprise culturing CAR-expressing immune cells alone and/or target antigen-expressing cells alone.

The period of co-culture can be, but not limited to, 1 to 21 days, preferably 1 to 14 days.

The ratio of the cell number of CAR-expressing immune cells to target antigen-expressing cells at the start of co-culture (CAR-expressing immune. cells/target antigen-expressing cells) is not particularly limited to, but can be for example, 0.05 to 20, preferably 0.1 to 10, more preferably 0.5 to 5, wherein the ratio is shown with the total number of cells to which a process for expressing a CAR or a target antigen is carried out. The cell density during co-culture can be, for example, $1 \times 10^6$ cells/mL to $100 \times 10^6$ cells/mL, when it is shown as the number of cells in the culture medium.

The medium used for co-culture or for preparation of CAR-expressing immune cells and/or target antigen-expressing cells is not particularly limited to, but can be, a medium used for conventional cell culture such as RPMI1640, MEM, X-VIVO, IMDM, DMEM, DC medium, or OptiMEM. The medium may be a medium to which serum (such as human serum or fetal bovine serum) is added according to conventional methods, or may be a serum-free medium. It is preferable to use a serum-free medium because it is highly safe for clinical application and the difference in culture efficiency between serum lots is unlikely to occur. Examples of serum-free media include TexMACS™ (Miltenyi Biotec), AIM V® (Thermo Fisher Scientific), and ALyS culture medium (Cell Science & Technology Institute, Inc.). When using serum, it is preferable to use autologous serum, that is, serum collected from an individual from which the CAR-expressing immune cells are derived (more specifically, a patient to which the cell population obtained by the production method of the present disclosure is to be administered). The basal medium is a medium suitable for cell culture, and can be TexMACS™, AIM V@, or ALyS culture medium (Cell Science & Technology Institute, Inc.) as described above. Other culture conditions are not limited as long as they are suitable for cell survival and proliferation and conventional conditions can be adopted. For example, the cells may be cultured in a $CO_2$ incubator ($CO_2$ concentration: 5%) set at 37° C.

A T cell growth factor or activator may be added to the medium to aid cell survival and proliferation. Examples of T cell growth factors include IL-1, IL-2, IL-7, IL-15, and IL-21, and examples of activators include anti-CD3 antibodies and anti-CD28 antibodies. For example, IL-2, an anti-CD3 antibody, and an anti-CD28 antibody may be added to the medium during co-culture. These factors are not essential, and especially when target antigen-expressing cells prepared from PBMCs are used, clinically applicable CAR-expressing immune cells can be efficiently obtained in a short period of time without addition of anti-CD3 antibodies and/or anti-CD28 antibodies. When preparing CAR-expressing immune cells, IL-7 and/or IL-15 may also be added to the medium. For example, IL-7 and IL-15 can be added to the medium at 5 ng/ml to 10 ng/ml, respectively. The T cell growth factor or activator can be prepared according to conventional methods, and commercially available products can also be used. The T cell growth factor or activator may be of a non-human animal species, but is preferably of human origin (and may be a recombinant one).

By co-culturing CAR-expressing immune cells and target antigen-expressing cells, it is possible to obtain a cell population containing CAR-expressing immune cells in a sufficient number and quality for clinical use. In particular, even when the target antigen is not expressed in blood cells (for example, in the case of tumor-related antigens of solid tumors such as HER2 and EPHB4), co-culturing CAR-expressing immune cells and target antigen-expressing cells provides appropriate stimulation from the target antigen-expressing cells to the CAR-expressing immune cells, and produces a cell population containing a sufficient number of CAR-expressing immune cells that have high cytotoxic activity and are not easily exhausted. The method of the present disclosure can efficiently produce a cell population expected to be highly effective compared to conventional methods. For example, the cell population obtained by the production method of the present disclosure may have a proportion of CAR-expressing immune cells of 20%, 30%, or 40% or more, preferably 40% or more. In addition, the cell population obtained by the production method of the present disclosure has low expression of PD-1, which is an exhaustion marker, and for example, the ratio of PD-1-expressing cells in CAR-expressing immune cells may be less than 10%, preferably less than 5%, more preferably less than 1%. Also, in the cell population obtained by the production method of the present disclosure, the proportion of naive cells in the CAR-expressing immune cells can be 45%, 50%, 55%, or 60% or more, preferably 60% or more.

Use of Cell Population

The cell population containing CAR-expressing immune cells produced by the method of the present disclosure can be used for the treatment of cancer, particularly for the treatment of cancer expressing the target antigen of the CAR-expressing immune cells. The cancer may be a solid tumor or a blood tumor. Specific examples of cancers include various B-cell lymphomas (e.g., follicular malignant lymphoma, diffuse large B-cell malignant lymphoma, mantle cell lymphoma, MALT lymphoma, intravascular B-cell lymphoma, CD20-positive Hodgkin lymphoma), myeloproliferative neoplasm, myelodysplastic/myeloproliferative neoplasm (CMML, JMML, CML, MDS/MPN-UC), myelodysplastic syndrome, acute myeloid leukemia, neuroblastoma, brain tumor, Ewing sarcoma, osteosarcoma, retinoblastoma, small cell lung cancer, non-small cell lung cancer, melanoma, bone and soft tissue sarcoma, kidney cancer, pancreatic cancer, malignant mesothelioma, prostate cancer, breast cancer, endometrial cancer, cervical cancer, ovarian cancer, and colon cancer, but are not limited thereto. In a preferred embodiment, the cancer is a solid tumor. Examples of solid tumors include, for example, neuroblastoma, brain tumor, Ewing sarcoma, osteosarcoma, retinoblastoma, small cell lung cancer, non-small cell lung cancer, melanoma, ovarian cancer, rhabdomyosarcoma, bone and soft tissue sarcoma, kidney cancer, pancreatic cancer, malignant mesothelioma, prostate cancer, breast cancer, endometrial cancer, cervical cancer, ovarian cancer, and colon cancer.

The cell population of the present disclosure is administered in a therapeutically effective amount appropriately determined according to factors such as age, body weight, and symptoms of the subject. The subject of the present disclosure is usually a human, preferably a cancer patient. The cell population of the present disclosure can be administered, for example, from $1\times10^4$ cells to $1\times10^{10}$ cells at a time. The administration route is not particularly limited to, but can be for example, intravenous injection, intraarterial injection, intraportal injection, intradermal injection, subcutaneous injection, intramuscular injection, or intraperitoneal injection. The cell population of the present disclosure may be administered systemically or locally, and the local administration includes direct injection into a target tissue, organ, or part. The administration schedule is appropriately determined according to factors such as age, body weight, and symptoms of the subject, and may be a single administration or a continuous or periodic multiple administrations.

In addition to the cell population to be administered to the subject, the composition comprising the cell population of the present disclosure may comprise a component such as dimethylsulfoxide (DMSO) or serum albumin for the purpose of protecting cells, an antibiotic for the purpose of preventing contamination by bacteria, or any of various components for the purpose of activating, proliferating or inducing differentiation of cells (such as vitamins, cytokines, growth factors, steroids). The composition can be prepared by conventional methods.

An exemplary embodiment of the present invention is described below.

[1] A method of producing a cell population containing Chimeric Antigen Receptor (CAR)-expressing immune cells, comprising co-culturing CAR-expressing immune cells and cells expressing a target antigen of the CAR, wherein the CAR-expressing immune cells are cells into which a CAR gene has been introduced and the target antigen-expressing cells are normal blood cells that have been engineered to express the target antigen.

[2] The method according to item 1, wherein the immune cells are lymphocytes.

[3] The method according to item 1 or 2, wherein the immune cells are T cells.

[4] The method according to any one of items 1 to 3, wherein the target antigen is HER2 or EPHB4.

[5] The method according to any one of items 1 to 4, wherein the CAR-expressing immune cells are cells that have been prepared by gene transfer into peripheral blood mononuclear cells (PBMCs).

[6] The method according to any one of items 1 to 5, further comprising preparing the CAR-expressing immune cells.

[7] The method according to item 6, wherein the CAR-expressing immune cells are prepared by gene transfer into PBMCs.

[8] The method according to item 6 or 7, wherein the CAR-expressing immune cells are prepared by the piggyBac transposon-mediated method.

[9] The method according to any one of items 1 to 8, wherein the target antigen-expressing cells are cells into which the target antigen gene has been introduced.

[10] The method according to any one of items 1 to 9, wherein the target antigen-expressing cells are cells into which one or more genes of one or more co-stimulatory molecules have been introduced.

[11] The method according to any one of items 1 to 10, wherein the target antigen-expressing cells are cells that have been prepared from PBMCs.

[12] The method according to item 11, wherein the target antigen-expressing cells are cells that have been prepared by gene transfer into PBMCs.

[13] The method according to item 12, wherein the gene transfer includes transfer of a target antigen gene.

[14] The method according to any one of items 1 to 13, further comprising preparing the target antigen-expressing cells.

[15] The method according to item 14, wherein the target antigen-expressing cells are prepared from PBMCs.

[16] The method according to item 15, wherein the target antigen-expressing cells are prepared by gene transfer into PBMCs.

[17] The method according to item 16, wherein the gene transfer includes transfer of a target antigen gene.

[18] The method according to any of items 10 to 17, wherein the one or more co-stimulatory molecules are selected from CD40, CD80, 4-1BBL, and OX40L.

[19] A cell population containing Chimeric Antigen Receptor (CAR)-expressing immune cells produced by the method according to any one of items 1 to 18.

[20] A composition for treating cancer comprising the cell population according to item 19.

[21] The composition according to item 20, wherein the cancer is a solid tumor.

[22] A method for treating cancer, comprising administering the cell population according to item 19 to a subject.

[23] A method for treating cancer, comprising producing a cell population by the method according to any one of items 1 to 18, and administering the cell population thus obtained to a subject.

[24] The cell population according to item 19 for use in treating cancer.

[25] Use of the cell population according to item 19 for the manufacture of a medicament for use in the treatment of cancer.

Hereinafter, the present invention will be further described with reference, to the examples. The present invention, however, is not limited to these examples in any sense.

EXAMPLES

Example 1

Figure 2:
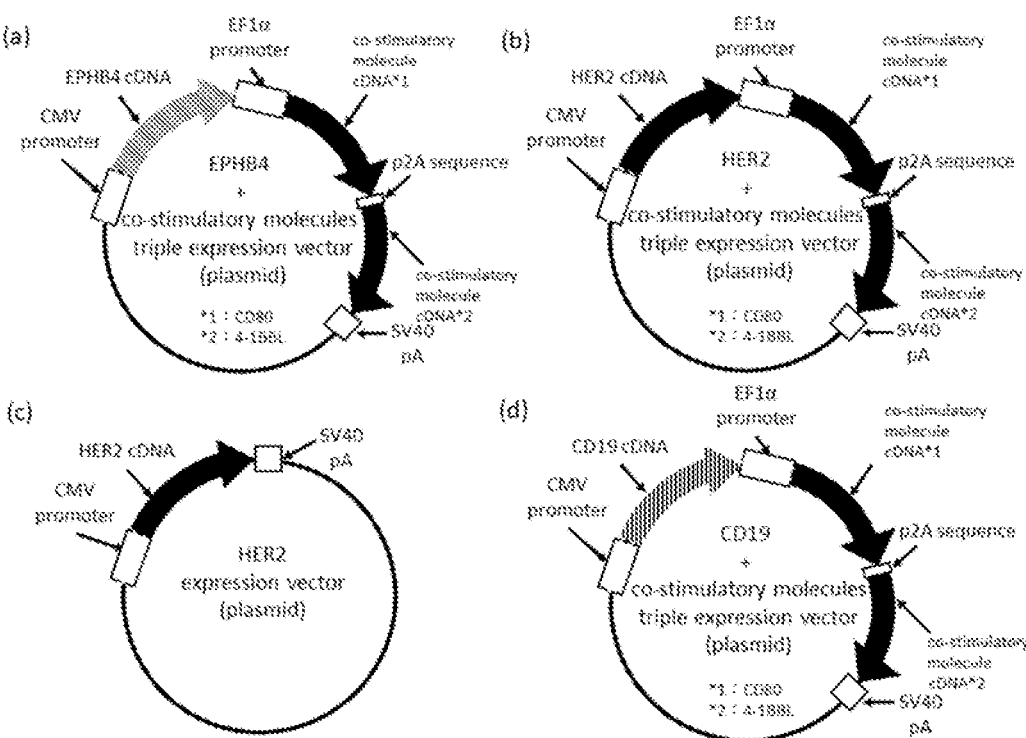
FIG. 2 shows the target antigen expression vector used in the example section.

Peripheral blood mononuclear cells (PBMCs) were separated and collected from peripheral blood by specific gravity separation centrifugation. Then, to $15 \times 10^6$ cells of the collected PBMCs, a vector to express EPHB4-CAR, which had an EPHB4 ligand (SEQ ID NO: 3) as an extracellular domain, and a spacer domain (SEQ ID NO: 6), a transmembrane domain (SEQ ID NO: 8), and an intracellular signal domain (SEQ ID NO: 9) (FIG. 1, (a)), and a transposase expression vector (FIG. 1, (c)) were introduced by gene transfer by electroporation to prepare EPHB4-CAR-expressing T cells. Also, to $5 \times 10^6$ PBMCs, a vector to express EPHB4 (SEQ ID NO: 11), which was the target molecule of EPHB4-CAR, and CD80 (SEQ ID NO: 12) and 4-1BBL (SEQ ID NO: 13) (FIG. 2, (a)) was introduced by electroporation to prepare EPHB4-expressing cells that transiently expressed EPHB4. The EPHB4-CAR-expressing T cells and EPHB4-expressing cells thus prepared were cultured separately for 1 day after the gene transfer, and then the EPHB4-expressing cells were irradiated with UV and $5 \times 10^6$ UV-irradiated EPHB4-expressing cells were divided and mixed with the EPHB4-CAR-expressing T cells on the first and third days of culture. The cells were co-cultured with ALyS culture solution containing IL-7 (10 ng/mL) and IL-15 (5 ng/mL) in the absence of IL-2, an anti-CD3 antibody and an anti-CD28 antibody, and collected 12 days after the start of the culture.

Comparative Example 1

In the same manner as in Example 1, PBMCs were collected and EPHB4-CAR-expressing T cells were prepared. Also, after UV irradiation to a part of the collected PBMCs, viral peptides (PepTivator CMV pp65, PepTivator AdV5 Hexon, PepTivator EBV EBNA-1, and PepTivator EBV BZLF1, Miltenyi Biotec) were added to the irradiated cells to prepare feeder cells. In addition, UV-irradiated Rh30 cells, which were cells of a cancer cell line expressing EPHB4, were prepared. Then, $10 \times 10^6$ EPHB4-CAR-expressing T cells were mixed with $2 \times 10^6$ feeder cells and $1 \times 10^6$ Rh30 cells and these cells were co-cultured with ALyS culture solution containing IL-7 (10 ng/mL) and IL-15 (5 ng/mL) in the presence an anti-CD3 antibody and an anti-CD28 antibody, and collected 9 days after the start of the culture.

Comparative Example 2

In the same manner as in Comparative Example 1, EPHB4-CAR-expressing T cells and UV-irradiated EPHB4-expressing Rh30 cells were prepared. Then, $10 \times 10^6$ EPHB4-CAR-expressing T cells and $1 \times 10^6$ Rh30 cells were mixed and co-cultured with ALyS culture solution containing IL-7 (10 ng/mL) and IL-15 (5 ng/mL) in the presence of an anti-CD3 antibody and an anti-CD28 antibody for 25 days, and the cells were collected after the culture.

Comparative Example 3

In the same manner as in Comparative Example 1, EPHB4-CAR-expressing T cells were prepared. Then, $10 \times 10^6$ EPHB4-CAR-expressing T cells were cultured with ALyS culture solution containing IL-7 (10 ng/mL) and IL-15

(5 ng/mL) in the presence of an anti-CD3 antibody and an anti-CD28 antibody for 25 days, and the cells were collected after the culture.

Test Example 1

For the cells obtained in Example 1 and Comparative Examples 1 to 3, the total number of cells was counted and the proportion of EPHB4-CAR-expressing T cells was analyzed by flow cytometry. The results are shown in Table 1.

TABLE 1

|  | Example 1 | Comparative example 1 | Comparative example 2 | Comparative example 3 |
|---|---|---|---|---|
| Culture period (day) | 112 | 9 | 25 | 25 |
| Cell number before culture ($\times 10^6$) | 15 | 10 | 10 | 10 |
| Cell number after culture ($\times 10^6$) | 53 | 3.4 | 7.0 | 5.6 |
| EPHB4-CAR-expressing T cells (%) | 47.1 | 1.0 | 0 | 0 |
| EPHB4-CAR-expressing T cell number ($\times 10^6$) | 25.0 | 0.03 | 0 | 0 |

As shown in Table 1, it was possible to culture EPHB4-CAR T cells only under the condition of Example 1. These results demonstrated that the production method comprising co-culturing EPHB4-expressing cells engineered to express the target antigen EPHB4 by introduction of an EPHB4 gene and EPHB4-CAR-expressing T cells was extremely useful.

Example 2

PBMCs were separated and collected in the same manner as in Example 1. To $10 \times 10^6$ cells of the collected PBMCs, a vector to express HER2-CAR, which had an anti-HER2scFV (SEQ ID NO: 1) as an extracellular domain, and a spacer domain (SEQ ID NO: 4), a transmembrane domain (SEQ ID NO: 7), and an intracellular signal domain (SEQ ID NO: 9) (FIG. 1, (b)) and a transposase expression vector (FIG. 1, (c)) were introduced by electroporation to prepare HER2-CAR-expressing T cells. Also, to $20 \times 10^6$ PBMCs, an expression vector to express HER2 (SEQ ID NO: 10), which was the target molecule of HER2-CAR, and CD80 (SEQ ID NO: 12) and 4-1BBL (SEQ ID NO: 13) (FIG. 2, (b)) was introduced by electroporation to prepare HER2-expressing cells that transiently expressed HER2. The HER2-CAR-expressing T cells and HER2-expressing cells thus prepared were cultured separately for 3 days after the gene transfer, and then the HER2-expressing cells were irradiated with UV and mixed with the HER2-CAR-expressing T cells. The cells were co-cultured with ALyS medium containing IL-7 (10 ng/mL) and IL-15 (5 ng/mL) as well as 2% artificial serum for 11 days in the absence of IL-2, an anti-CD3 antibody and an anti-CD28 antibody, and collected 14 days after the start of the culture.

Comparative Example 4

PBMCs were separated and collected in the same manner as in Example 1. To $15 \times 10^6$ cells of the collected PBMCs, a HER2-CAR expression vector (FIG. 1, (b)) and a transposase expression vector (FIG. 1, (c)) were introduced by electroporation to prepare HER2-CAR-expressing T cells. Also, after UV irradiation to $2 \times 10^6$ PBMCs, viral peptides (PepTivator CMV pp65, PepTivator AdV5 Hexon, PepTivator EBV EBNA-1, and PepTivator EBV BZLF1, Miltenyi Biotec) were added to prepare feeder cells. Then, $15 \times 10^6$ HER2-CAR-expressing T cells thus prepared were cultured for 7 days on a plate on which the target molecule of HER2-CAR, HER2 protein, was immobilized at 100 µg/mL, with ALyS medium containing IL-7 (10 ng/mL) and IL-15 (5 ng/mL) as well as 2% artificial serum, and then mixed with the feeder cells. The cells were co-cultured for another 7 days, and collected 14 days after the start of the culture.

Test Example 2

For the cells obtained in Example 2 and Comparative Example 4, the total number of cells was counted, and the proportion of HER2-CAR-expressing T cells was analyzed by flow cytometry. The results are shown in Table 2.

TABLE 2

|  | Example 2 | Comparative example 4 |
|---|---|---|
| Cell number before culture ($\times 10^6$) | 10 | 15 |
| Cell number after culture ($\times 10^6$) | 146 | 11 |
| HER2-CAR-expressing T cells (%) | 34.1 | 33.7 |
| HER2-CAR-expressing T cell number ($\times 10^6$) | 49.8 | 3.7 |

As shown in Table 2, it was possible to obtain a sufficient number of HER2-CAR-expressing T cells for clinical use in Example 2, although the number of HER2-CAR-expressing T cells prepared before the start of culture was smaller than that in Comparative Example 4. These results demonstrated that the production method comprising co-culturing HER2-expressing cells engineered to express the target antigen HER2 by introduction of an HER2 gene and HER2-CAR-expressing T cells was extremely useful.

Example 3

PBMCs were separated and collected in the same manner as in Example 1. Then, to $20 \times 10^6$ cells of the collected PBMCs, the HER2-CAR expression vector (FIG. 1, (b)) and the transposase expression vector (FIG. 1, (c)) as used in Example 2 were introduced by electroporation to prepare HER2-CAR-expressing T cells. Also, to $20 \times 10^6$ PBMCs, an expression vector to express HER (SEQ ID NO: 10), which was the target molecule of HER2-CAR, (FIG. 2, (c)) was introduced by electroporation to prepare HER2-expressing cells that transiently expressed HER2 (SEQ ID NO: 10). The HER2-CAR-expressing T cells and HER2-expressing cells thus prepared were cultured separately for 1 day after the gene transfer, and then the HER2-expressing cells were irradiated with UV and mixed with the HER2-CAR-expressing T cells. The cells were co-cultured in the presence of IL-2, an anti-CD3 antibody and an anti-CD28 antibody, and collected 14 days after the start of the culture.

Comparative Example 5

HER2-CAR-expressing T cells were prepared in the same manner as in Example 3. Also, to $20 \times 10^6$ PBMCs, instead of the HER2 expression vector, a vector expressing EPHB4 (SEQ ID NO: 11) and CD80 (SEQ ID NO: 12) and 4-1BBL (SEQ ID NO: 13) (FIG. 2, (a)) was introduced by electroporation to prepare EPHB4-expressing cells to be used as antigen-presenting cells. The HER2-CAR-expressing T cells and EPHB4-expressing cells thus prepared were co-cultured in the same manner as in Example 3, and the cells were collected 14 days after the start of the culture.

Comparative Example 6

HER2-CAR-expressing T cells were prepared in the same manner as in Example 3. The HER2-CAR-expressing T cells thus prepared were co-cultured with $1 \times 10^6$ U2OS cells, which were cells of a cancer cell line expressing HER2 and used as antigen-presenting cells instead of the HER2-expressing cells, in the same manner as in Example 3. The cells were collected 14 days after the start of the culture.

Example 4

PBMCs were separated and collected in the same manner as in Example 1. Then, to $20 \times 10^6$ cells of the collected PBMCs, the EPHB4-CAR expression vector (FIG. 1, (a)) and the transposase expression vector (FIG. 1, (c)) as used in Example 1 were introduced by electroporation to prepare EPHB4-CAR-expressing T cells. Also, to $20 \times 10^6$ PBMCs, an expression vector to express EPHB4 (SEQ ID NO: 11), which was the target molecule of EPHB4-CAR, and CD80 (SEQ ID NO: 12) and 4-1BBL (SEQ ID NO: 13) was introduced by electroporation to prepare EPHB4-expressing cells that transiently express EPHB4. The EPHB4-CAR-expressing T cells and EPHB4-expressing cells thus prepared were cultured separately for 1 day after the gene transfer, and then the EPHB4-expressing cells were irradiated with UV and mixed with EPHB4-CAR-expressing T cells. The cells were co-cultured in the absence of IL-2, an anti-CD3 antibody and an anti-CD28 antibody, and collected 14 days after the start of culture.

Comparative Example 7

EPHB4-CAR-expressing T cells were prepared in the same manner as in Example 4. To $20 \times 10^6$ PBMCs, a vector to express CD19 (SEQ ID NO: 16) instead of EPHB4 and CD80 (SEQ ID NO: 12) and 4-1BBL (SEQ ID NO: 13) (FIG. 2, (d)) was introduced by electroporation to prepare CD19-expressing cells to be used as antigen-presenting cells. The EPHB4-CAR-expressing T cells and CD19-expressing cells thus prepared were co-cultured in the same manner as in Example 4, and the cells were collected 14 days after the start of the culture.

Test Example 3

For the cells obtained in Examples 3 and 4 and Comparative Examples 5 to 7, respectively, the total number of cells was counted, and the proportion of CAR-expressing T cells was analyzed by flow cytometry. The results are shown in Table 3.

TABLE 3

| | CAR-T cells | Antigen presenting cells | CAR-T cells (%) | Total cell number ($\times 10^6$) | CAR-T cell number ($\times 10^6$) |
|---|---|---|---|---|---|
| Example 3 | HER2 | HER2-expressing PBMCs | 28.2 | 90 | 25.4 |
| Comparative example 5 | HER2 | EPHB4, CD80, 4-1BBL-expressing PBMCs | 1.3 | 5.8 | 0.1 |
| Comparative example 6 | HER2 | U2OS (expressing HER2) | 10.2 | 5.5 | 0.6 |
| Example 4 | EPHB4 | EPHB4, CD80, 4-1BBL-expressing PBMCs | 11.2 | 85.6 | 9.6 |
| Comparative example 7 | EPHB4 | CD19, CD80, 4-1BBL-expressing PBMCs | 15.3 | 3 | 0.5 |

As shown in Table 3, it was not possible to produce a sufficient number of CAR-T cells by culture when cancer cells expressing the target molecule of HER2 were used as antigen-presenting cells (Comparative Example 6), and when antigen presenting cells expressed a target antigen that did not match the CAR of CAR-T cells (Comparative Examples 5 and 7). In contrast, it was possible to produce a sufficient number of CAR-T cells for clinical use when cells engineered to express the target antigen that matched the CAR of CAR-T cells were used as antigen-presenting cells (Examples 3 and 4).

Test Example 4

In order to confirm the characteristics of the CAR-expressing immune cells produced by the production method of the present disclosure, CAR-expressing immune cells were produced as follows. First, peripheral blood mononuclear cells (PBMCs) were separated and collected from peripheral blood by specific gravity separation centrifugation. To $20 \times 10^6$ cells of the collected PBMCs, the HER2-CAR expression vector (FIG. 1, (b)) and the transposase expression vector (FIG. 1, (c)) as used in Example 2 were introduced by electroporation to prepare HER2-CAR-expressing T cells. Also, in order to prepare target antigen-expressing cells, to $10 \times 10^6$ PBMCs, an expression vector to express HER2 (SEQ ID NO: 10), which was the target molecule of HER2-CAR, and any one (FIG. 3, (a)) or two (FIG. 2, (b); FIG. 3, (b)) of CD80 (SEQ ID NO: 12), 4-1BBL (SEQ ID NO: 13), CD40 (SEQ ID NO: 14) and OX40 ligand (SEQ ID NO: 15) was introduced by electroporation to prepare HER2-expressing cells that transiently expressed HER2. The HER2-CAR-expressing T cells and HER2-expressing cells thus prepared were cultured for 1 day after the gene transfer. Then, the HER2-expressing cells were irradiated with UV, and $10 \times 10^6$ HER2-expressing cells were mixed with $20 \times 10^6$ HER2-CAR-expressing T cells. The cells were co-culture in the absence of IL-2, an anti-CD3 antibody and an anti-CD28 antibody, and collected 14 days after the start of culture. The number of cells obtained is shown in Table 4.

TABLE 4

| CAR-expressing | HER2-CAR-expressing T cells | | | | | |
|---|---|---|---|---|---|---|
| immune cells<br>Target antigen-<br>expressing cells | HER2<br>CD80<br>4-1BBL | HER2<br>CD80 | HER2<br>4-1BBL | HER2<br>CD40<br>OX40L | HER2<br>CD40 | HER2<br>OX40L |
| Cell number<br>obtained (×10⁷) | 23.5 | 22.8 | 21.5 | 17 | 19.8 | 21.9 |

Regarding the HER2-CAR-expressing T cells thus obtained, the proportion of cells expressing any of a T cell marker, CD3; the introduced HER2-CAR; an exhaustion marker, PD-1; and markers for analysis of naive T cells or central memory T cells, CCR7 and CD45RA was analyzed by flow cytometry. The results are shown in FIGS. 4 and 5.

Also, a killing assay was performed using the obtained HER2-CAR-expressing T cells. First, U2OS cells, which were cells of a cancer cell line expressing HER2, were seeded on a plate for a real-time cell analyzer (xCELLigence, ACEA Bioscience, Inc.) at $1 \times 10^4$ cells/well and allowed to attach the plate. Next, respective HER2-CAR-expressing T cells were seeded on the plate so that the ratio of HER2-CAR-expressing T cells to U2OS cells was 1: 2, and the cells were co-cultured for 72 hours to determine the ratio of injured U2OS cells with a real-time cell analyzer. After that, the HER2-CAR-expressing T cells co-cultured with the U2OS cells were added to U2OS cells prepared in another well, and the cells were co-cultured for another 72 hours. Then, the step of measuring cytotoxic activity was performed three times in total. The results are shown in FIGS. 6 and 7.

Figure 4:
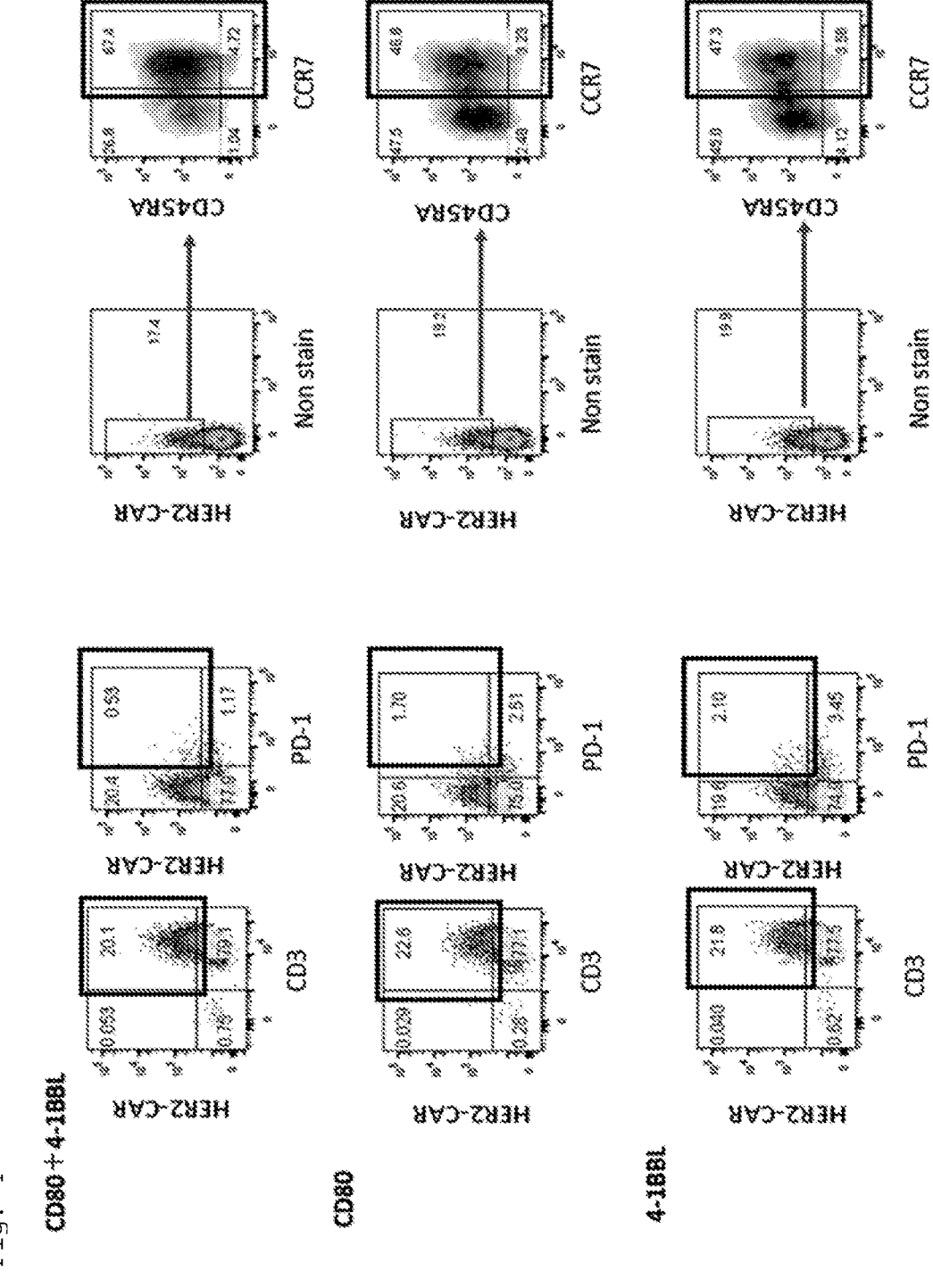
FIG. 4 shows the results of flow cytometric analysis of HER2-CAR, CD3, PD-1, CCR7 and CD45RA expressions in HER2-CAR-expressing T cells co-cultured with target antigen-expressing cells that express HER2 and a co-stimulatory molecule(s) (CD80+4-1BBL, CD80, or 4-1BBL).
Figure 5:
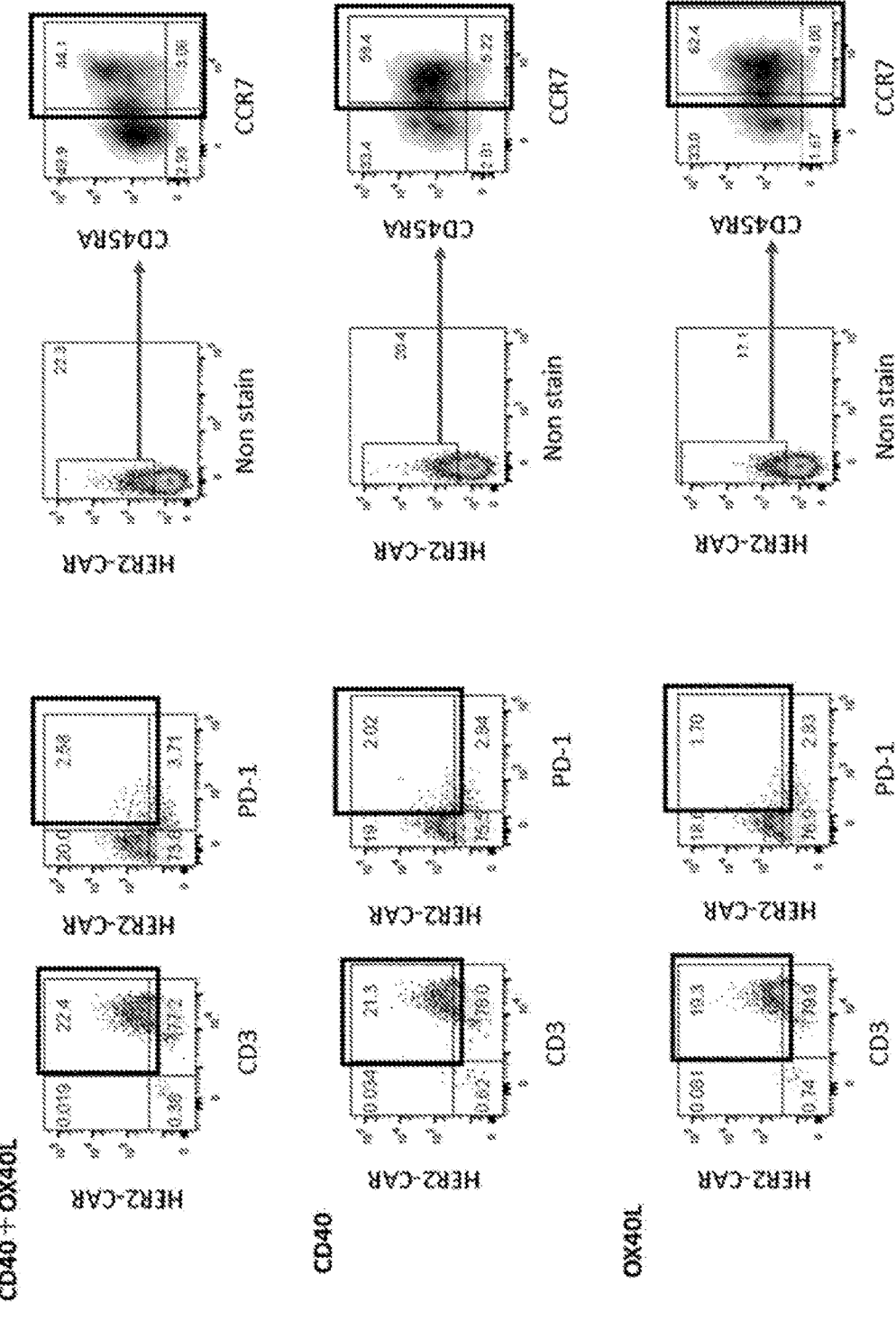
FIG. 5 shows the results of flow cytometric analysis of HER2-CAR, CD3, PD-1, CCR7 and CD45RA expressions in HER2-CAR-expressing T cells co-cultured with target antigen-expressing cells that express HER2 and a co-stimulatory molecule(s) (CD40+OX40L, CD40, or OX40L).

As shown with the results in FIGS. 4 and 5, the HER2-CAR-expressing T cells obtained by the production method of the present disclosure accounted for 20% or more of the total number of cells, indicating that HER2-CAR-expressing T cells were obtained at a high proportion. The proportion of cells expressing PD-1, which was an exhaustion marker of these T cells, was very small. Also, the proportion of naive T cells (CD45RA positive and CCR7 positive) and central memory T cells (CD45RA negative and CCR7 positive) in the HER2-CAR-expressing T cells was high and at least 45% or more in total.

Figures 6, 7:
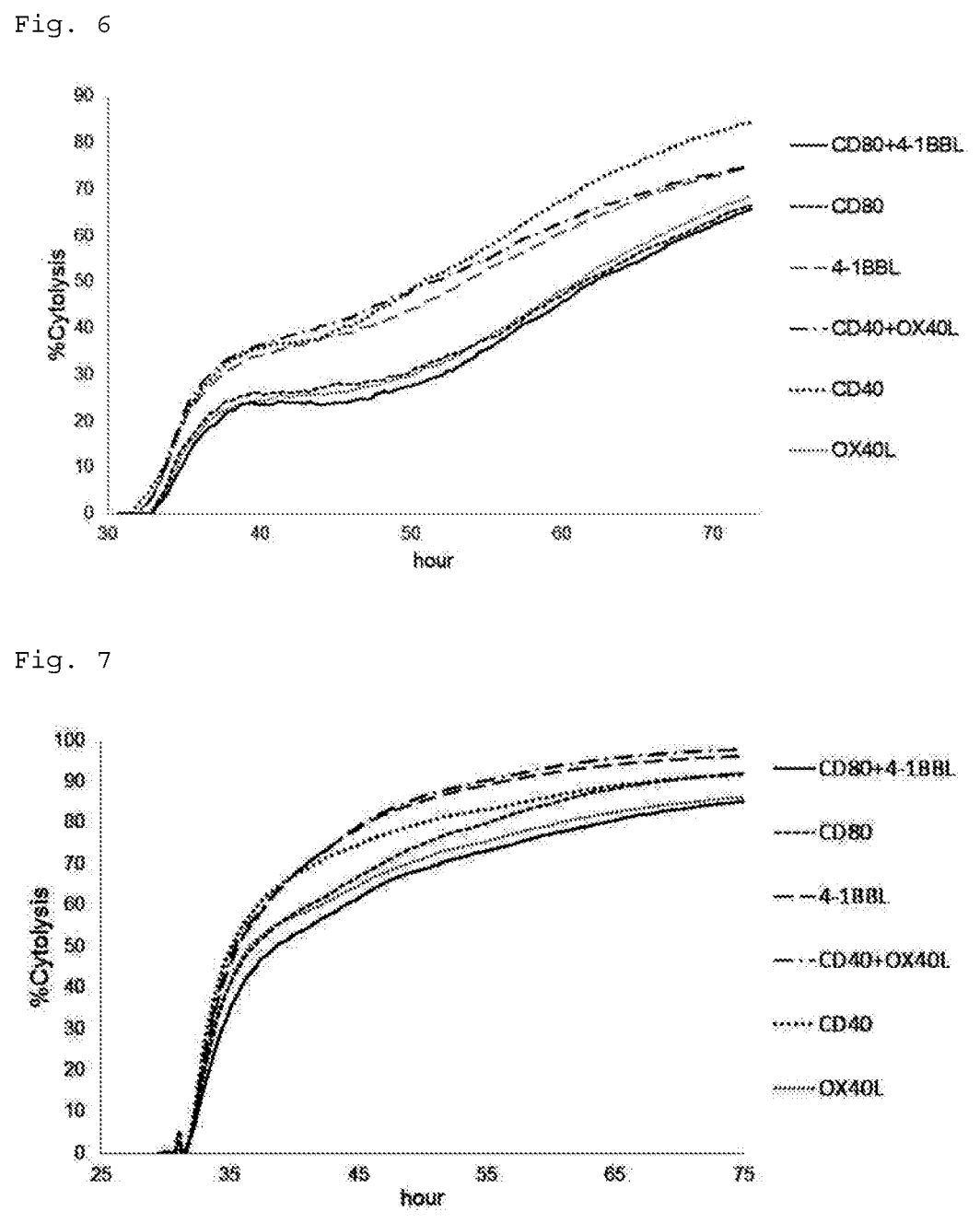

Further, from the results of FIGS. 6 and 7, it was found that the HER2-CAR-expressing T cells of the present disclosure showed excellent cytotoxic activity against the HER2-expressing cancer cell line, and that the cells did not become exhausted in two consecutive measurements of killing activity and had sufficient cytotoxic activity even in the second killing activity measurement.

From these results, it was found that the production method of the present disclosure could efficiently produce a high-quality cell population containing a large number of cells having a low expression of the exhaustion marker and a phenotype of naive T cells or central memory T cells, and it was particularly effective in the production of CAR-introduced immune cells for solid tumors.

Example 5

PBMCs were separated and collected from peripheral blood by specific gravity separation centrifugation. Then, to $20 \times 10^6$ cells of the collected PBMCs, the HER2-CAR expression vector (FIG. 1, (b)) and the transposase expression vector (FIG. 1, (c)) as used in Example 2 were introduced by electroporation to prepare HER2-CAR-expressing T cell. Also, to $10 \times 10^6$ PBMCs, an expression vector to express HER2 (SEQ ID NO: 10), which was the target molecule of HER2-CAR, and CD80 (SEQ ID NO: 12) and 4-1BBL (SEQ ID NO: 13) (FIG. 2, (d)) was introduced by electroporation to prepare HER2-expressing cells that transiently expressed HER2. The HER2-CAR-expressing T cells and the HER2-expressing cells thus prepared were cultured separately for 1 day after the gene transfer, and then the HER2-expressing cells were irradiated with UV and mixed with the HER2-CAR-expressing T cells. The cells were co-cultured in the absence of IL-2, an anti-CD3 antibody and an anti-CD28 antibody, and collected 14 days after the start of culture.

Example 6

PBMCs were separated and collected from peripheral blood by specific gravity separation centrifugation. Then, to $40 \times 10^6$ PBMCs, an expression vector to express CD19-CAR, which had an anti-CD19scFV (SEQ ID NO: 2) as an extracellular domain, and a spacer domain (SEQ ID NO: 5), a transmembrane domain (SEQ ID NO: 7), and an intracellular signal domain (SEQ ID NO: 9) (FIG. 1, (d)) and a transposase expression vector (FIG. 1, (c)) were introduced by electroporation to prepare CD19-CAR-expressing T cells. Also, to $10 \times 10^6$ PBMCs, an expression vector to express CD19 (SEQ ID NO: 16), which was the target molecule of CD19-CAR, and CD80 (SEQ ID NO: 12) and 4-1BBL (SEQ ID NO: 13) (FIG. 2, (d)) was introduced by electroporation to prepare CD19-expressing cells that transiently expressed CD19. The CD19-CAR-expressing T cells and the CD19-expressing cells thus prepared were cultured separately for 1 day after the gene transfer, and then the CD19-expressing cells were irradiated with UV and mixed with the CD19-CAR-expressing T cells. The cells were co-cultured in the absence of IL-2, an anti-CD3 antibody and an anti-CD28 antibody, and collected 14 days after the start of culture.

Comparative Example 8

PBMCs were separated and collected from peripheral blood by specific gravity separation centrifugation. Then, $0.125 \times 10^6$ PBMCs were stimulated with an anti-CD3 antibody and an anti-CD28 antibody, and subjected to gene transfer using a retroviral vector having the same HER2-CAR expression unit as in Example 2 (FIG. 3 ($c$)). The cells were cultured in the absence of IL-2, and collected 14 days after the start of the culture.

Test Example 5

Killing assays were performed using the CAR-expressing T cells obtained in Example 5, Example 6, and Comparative Example 8. First, U2OS cells, which were cells of a cancer cell line expressing HER2, were seeded on a plate for a real-time cell analyzer (xCELLigence, ACEA Bioscience, Inc.) at 5000 cells/well, and allowed to attach the plate. Then, respective CAR-expressing T cells obtained in Example 5, Example 6, and Comparative Example 8 were seeded on the plate so that the ratio of the number of CAR-expressing T cells to U2OS cells was 4: 1. The cells were co-cultured for 100 hours and the proportion of injured U2OS cells was measured with a real-time cell analyzer. The results are shown in FIG. 8.

Figure 8:
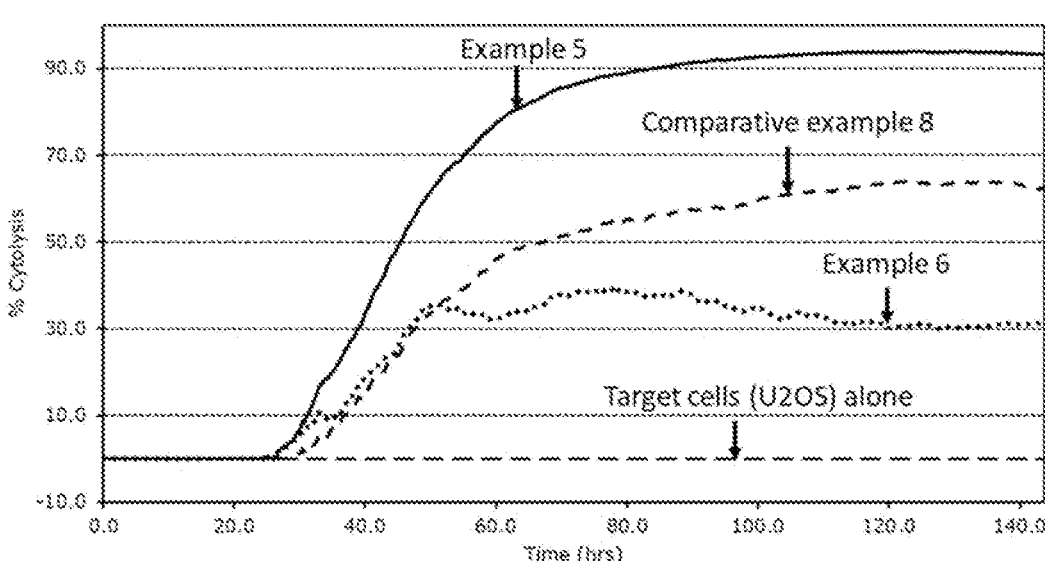
FIG. 8 shows the results of the killing assay targeting HER-expressing U2OS cells with HER2-CAR-expressing T cells of Example 5, CD19-CAR-expressing T cells of Example 6, and HER2-CAR-expressing T cells of Comparative Example 8.

As shown with the results in FIG. 8, the HER2-CAR-expressing T cells of Example 5 injured 95% or more of the HER2-expressing U2OS cells 72 hours after the start of co-culture, whereas the cytotoxicity of the HER2-CAR-expressing T cells of Comparative Example 8 was about 65%. Also, in the CD19-CAR-expressing T cells of Example 6, non-specific cytotoxic reaction of about 30% to HER-expressing U2OS cells was observed. Therefore, it was considered that the CAR-dependent specific cytotoxic activity was weak in the CAR-T cells prepared in Comparative Example 8. From these results, it was considered that the HER2-CAR-expressing T cells obtained by the production method of the present disclosure had a strong CAR-specific cytotoxic activity.

Example 7

PBMCs were separated and collected from a healthy subject. Then, to $20 \times 10^6$ cells of the collected PBMCs, the HER2-CAR expression vector (FIG. 1, (b)) and the transposase expression vector (FIG. 1, (c)) as used in Example 2 were introduced by electroporation to prepare HER2-CAR-expressing T cells. Also, to $20 \times 10^6$ PBMCs, an expression vector to express HER2 (SEQ ID NO: 10), which was the target molecule of HER2-CAR, (FIG. 2, (c)) was introduced by electroporation to prepare HER2-CAR-expressing T cells that transiently expressed HER2 (SEQ ID NO: 10). The HER2-CAR-expressing T cells and the HER2-expressing cells thus prepared were cultured separately for 1 day after the gene transfer, and then the HER2-expressing cells were irradiated with UV and mixed with the HER2-CAR-expressing T cells. The cells were co-cultured in the absence of IL-2, an anti-CD3 antibody and an anti-CD28 antibody, and collected 14 days after the start of culture.

Comparative Example 9

In the same manner as in Example 7, to $10 \times 10^6$ PBMCs, the HER2-CAR expression vector and the transposase expression vector were introduced by electroporation to prepare HER2-CAR-expressing T cells. Then, $3 \times 10^6$ PBMCs collected from the same healthy subject were irradiated with UV and mixed with the HER2-CAR-expressing T cells thus prepared. The cells were co-cultured in the same manner as in Example 7, and collected 14 days after the start of culture.

Test Example 6

For the cells obtained in Example 7 and Comparative Example 9, respectively, the total number of cells was counted and the proportion of CAR-expressing T cells was analyzed by flow cytometry. The results are shown in Table 5.

TABLE 5

| | | Cell number ($\times 10^6$ cells) | | Cell growth rate | CAR⁺ | CAR⁺ cells ($\times 10^6$ |
|---|---|---|---|---|---|---|
| | AP condition | day 0 | day 14 | (%) | (%) | cells) |
| Example 7 | PBMCs with AP-tHER2.CD80.BBL | 20 | 151.7 | 758.5 | 52.6 | 61.20 |
| Comparative example 9 | PBMCs alone | 8 | 3.7 | 45.6 | 8.4 | 0.02 |

As shown with the results in Table 5, it was not possible to produce a sufficient number of CAR-T cells by culture when the cells were simply co-cultured with PBMCs (Comparative Example 9). In contrast, the production method of the present invention was able to produce a sufficient number of CAR-T cells for clinical application (Example 7).

Example 8

PBMC were separated and collected from a healthy subject. Then, to $17 \times 10^6$ cells of the collected PBMCs, the HER2-CAR expression vector (FIG. 1, (b)) and the transposase expression vector (FIG. 1, (c)) as used in Example 2 were introduced by electroporation to prepare HER2-CAR-expressing T cells. Also, to $17 \times 10^6$ PBMCs, an expression vector to express HER2 (SEQ ID NO: 10), which was the target molecule of HER2-CAR, (FIG. 2, (c)) was introduced by electroporation to prepare HER2-expressing cells that transiently expressed HER2 (SEQ ID NO: 10). The HER2-CAR-expressing T cells and the HER2-expressing cells thus prepared were separately cultured for 1 day after the gene transfer, and then the HER2-expressing cells were irradiated with UV and mixed with the HER2-CAR-expressing T cells. The cells were co-cultured in the absence of IL-2, an anti-CD3 antibody and an anti-CD28 antibody, and collected 14 days after the start of culture.

Comparative Example 10

In the same manner as in Example 8, to $17 \times 10^6$ PBMCs, the HER2-CAR expression vector and the transposase expression vector were introduced by electroporation to prepare HER2-CAR-expressing T cells. Also, in the same manner except that $17 \times 10^6$ K562 cells (not expressing HER2) were used instead of PBMCs, the HER2 expression vector was introduced into the cells to prepare HER2-expressing cells. The HER2-expressing cells thus prepared were irradiated with UV and mixed with the HER2-CAR-expressing T cells. The cells were co-cultured in the same manner as in Example 8, and were collected 14 days after the start of culture.

Comparative Example 11

In the same manner as in Example 8, to $17 \times 10^6$ PBMCs, the HER2-CAR expression vector and the transposase expression vector were introduced by electroporation to prepare HER2-CAR-expressing T cells. Also, in the same manner except that $10 \times 10^6$ Rh30 cells (expressing HER2) were used instead of PBMCs, the HER2 expression vector was introduced into the cells to prepare HER2-expressing cells. The HER2-expressing cells thus prepared were irradiated with UV and mixed with the HER2-CAR-expressing T cells. The cells were co-cultured in the same manner as in Example 8, and were collected 14 days after the start of culture.

Test Example 6

For the cells obtained in Example 8 and Comparative Examples 10 and 11, respectively, the total number of cells was counted and the proportion of CAR-expressing T cell was analyzed by flow cytometry. The results are shown in Table 6.

TABLE 6

| | AP condition | Cell number (×10⁶) | | Cell growth rate (%) | CAR⁺ (%) | CD8⁺ cells/ CAR⁺ cells (%) | PD-1- expressing cells/ CAR⁺ cells (%) | Naïve cells*/ CAR⁺ cells (%) | CAR⁺ cells (×10⁶ cells) | CD8⁺, CAR⁺ cells (×10⁶ cells) |
|---|---|---|---|---|---|---|---|---|---|---|
| | | day 0 | day 14 | | | | | | | |
| Example 8 | PBMCs with AP-tHER2.CD80.BBL | 17 | 170 | 997.1 | 62.3 | 58.7 | 0.7 | 62.8 | 106 | 62 |
| Comparative example 10 | K562 with AP-tHER2.CD80.BBL | 17 | 31 | 183.5 | 85.2 | 21.8 | 23.4 | 40.1 | 27 | 6 |
| Comparative example 11 | Rh30 with AP-tHER2.CD80.BBL | 17 | 13 | 78.8 | 62.2 | 18.3 | 10.3 | 42.3 | 8 | 2 |

*CD45RA-positive, CCR7-positive cells

As shown in Table 6, by using HER2-expressing cells prepared by subjecting PBMCs to express the target antigen HER2, 5 times or more cells were obtained as compared with the cells obtained by using K562 and Rh30 cells of the comparative examples. Therefore, it was found that the method of the present disclosure showed excellent cell productivity and enabled production of a sufficient number of cells necessary for clinical use. In particular, the proportion of CD8-positive cells was 58.7% when the cells prepared from PBMCs were used as HER2-expressing cells and it was more than twice as high as the proportion when K562 or Rh30 cells were used, and the number of CAR-positive, CD8-positive cells obtained was more than 10 times higher. It was found that CD8-positive CAR-T cells could be produced predominantly.

Further, in terms of quality, when cells prepared from PBMCs were used as HER2-expressing cells, the expression of PD-1 in CAR-positive cells was extremely low at 0.7% as compared with the expression when K562 or Rh30 cells were used, and the proportion of naive cells positive for CD45RA and CCR7 was also 62.8%, which was more than 1.5 times higher, indicating that the cells were young and not exhausted and high-quality CAR-T cells could be produced.

INDUSTRIAL APPLICABILITY

According to the present disclosure, the cell proliferation rate in the production of CAR-expressing immune cells can be increased, and CAR-T cells having high cytotoxic activity can be stably produced. In particular, the production efficiency of CAR-expressing immune cells for solid tumors can be dramatically improved, and thus CAR-T cell therapies can be applied to various cancer types.

The invention claimed is:

1. A method of producing a cell population containing Chimeric Antigen Receptor (CAR)-expressing immune cells, comprising co-culturing CAR-expressing immune cells and cells expressing a target antigen of the CAR, wherein the CAR-expressing immune cells are cells into which a CAR gene has been introduced and the target antigen-expressing cells are cells that have been prepared by gene transfer into peripheral blood mononuclear cells (PBMCs), wherein the target antigen is Human epidermal growth factor receptor 2 (HER2) or Ephrin type-B receptor 4 (EPHB4).

2. The method according to claim 1, wherein the immune cells are lymphocytes.

3. The method according to claim 1, wherein the immune cells are T cells.

4. The method according to claim 1, wherein the CAR-expressing immune cells are cells that have been prepared by gene transfer into peripheral blood mononuclear cells (PBMCs).

5. The method according to claim 1, further comprising preparing the CAR-expressing immune cells.

6. The method according to claim 5, wherein the CAR-expressing immune cells are prepared by gene transfer into PBMCs.

7. The method according to claim 5, wherein the CAR-expressing immune cells are prepared by the piggyflac transposon-mediated method.

8. The method according to claim 1, wherein the target antigen-expressing cells are cells into which one or more genes of one or more co-stimulatory molecules have been introduced.

9. The method according to claim 1, wherein the gene transfer includes transfer of a target antigen gene.

10. The method according to claim 1, further comprising preparing the target antigen-expressing cells.

11. The method according to claim 10, wherein the target antigen-expressing cells are prepared from PBMCs.

12. The method according to claim 11, wherein the target antigen-expressing cells are prepared by gene transfer into PBMCs.

13. The method according to claim 12, wherein the gene transfer includes transfer of a target antigen gene.

14. The method according to claim 8, wherein the one or more co-stimulatory molecules are selected from CD40, CD80, 4-1BBL, and OX40L.

15. A cell population containing Chimeric Antigen Receptor (CAR)-expressing immune cells produced by the method according to claim 1.

16. A method for treating cancer, comprising administering the cell population according to claim 15 to a subject.

17. The method according to claim 16, wherein the cancer is a solid tumor.

* * * * *

SEQUENCE LISTING

```
<160> NUMBER OF SEQ ID NOS: 16

<210> SEQ ID NO 1
<211> LENGTH: 262
<212> TYPE: PRT
<213> ORGANISM: Artificial Sequence
<220> FEATURE:
<223> OTHER INFORMATION: HER2-scFv

<400> SEQUENCE: 1

Met Asp Trp Ile Trp Arg Ile Leu Phe Leu Val Gly Ala Ala Thr Gly
1               5                   10                  15

Ala His Ser Glu Val Gln Leu Gln Gln Ser Gly Pro Glu Leu Lys Lys
            20                  25                  30

Pro Gly Glu Thr Val Lys Ile Ser Cys Lys Ala Ser Gly Tyr Pro Phe
            35                  40                  45

Thr Asn Tyr Gly Met Asn Trp Val Lys Gln Ala Pro Gly Gln Gly Leu
        50                  55                  60

Lys Trp Met Gly Trp Ile Asn Thr Ser Thr Gly Glu Ser Thr Phe Ala
65                  70                  75                  80

Asp Asp Phe Lys Gly Arg Phe Asp Phe Ser Leu Glu Thr Ser Ala Asn
                85                  90                  95

Thr Ala Tyr Leu Gln Ile Asn Asn Leu Lys Ser Glu Asp Met Ala Thr
            100                 105                 110

Tyr Phe Cys Ala Arg Trp Glu Val Tyr His Gly Tyr Val Pro Tyr Trp
            115                 120                 125

Gly Gln Gly Thr Thr Val Thr Val Ser Ser Gly Gly Gly Gly Ser Gly
        130                 135                 140
```

-continued

```
Gly Gly Gly Ser Gly Gly Gly Ser Asp Ile Gln Leu Thr Gln Ser
145             150             155             160

His Lys Phe Leu Ser Thr Ser Val Gly Asp Arg Val Ser Ile Thr Cys
            165             170             175

Lys Ala Ser Gln Asp Val Tyr Asn Ala Val Ala Trp Tyr Gln Gln Lys
            180             185             190

Pro Gly Gln Ser Pro Lys Leu Leu Ile Tyr Ser Ala Ser Ser Arg Tyr
            195             200             205

Thr Gly Val Pro Ser Arg Phe Thr Gly Ser Gly Ser Gly Pro Asp Phe
            210             215             220

Thr Phe Thr Ile Ser Ser Val Gln Ala Glu Asp Leu Ala Val Tyr Phe
225             230             235             240

Cys Gln Gln His Phe Arg Thr Pro Phe Thr Phe Gly Ser Gly Thr Lys
            245             250             255

Leu Glu Ile Lys Ala Leu
            260
```

```
<210> SEQ ID NO 2
<211> LENGTH: 274
<212> TYPE: PRT
<213> ORGANISM: Artificial Sequence
<220> FEATURE:
<223> OTHER INFORMATION: CD19-scFv

<400> SEQUENCE: 2
```

```
Met Glu Phe Gly Leu Ser Trp Leu Phe Leu Val Ala Ile Leu Lys Gly
1               5               10              15

Val Gln Cys Ser Arg Asp Ile Gln Met Thr Gln Thr Thr Ser Ser Leu
            20              25              30

Ser Ala Ser Leu Gly Asp Arg Val Thr Ile Ser Cys Arg Ala Ser Gln
            35              40              45

Asp Ile Ser Lys Tyr Leu Asn Trp Tyr Gln Gln Lys Pro Asp Gly Thr
            50              55              60

Val Lys Leu Leu Ile Tyr His Thr Ser Arg Leu His Ser Gly Val Pro
65              70              75              80

Ser Arg Phe Ser Gly Ser Gly Ser Gly Thr Asp Tyr Ser Leu Thr Ile
                85              90              95

Ser Asn Leu Glu Gln Glu Asp Ile Ala Thr Tyr Phe Cys Gln Gln Gly
            100             105             110

Asn Thr Leu Pro Tyr Thr Phe Gly Gly Gly Thr Lys Leu Glu Leu Lys
            115             120             125

Arg Gly Gly Gly Gly Ser Gly Gly Gly Gly Ser Gly Gly Gly Gly Ser
            130             135             140

Gly Gly Gly Gly Ser Glu Val Gln Leu Gln Gln Ser Gly Pro Gly Leu
145             150             155             160

Val Ala Pro Ser Gln Ser Leu Ser Val Thr Cys Thr Val Ser Gly Val
            165             170             175

Ser Leu Pro Asp Tyr Gly Val Ser Trp Ile Arg Gln Pro Pro Arg Lys
            180             185             190

Gly Leu Glu Trp Leu Gly Val Ile Trp Gly Ser Glu Thr Thr Tyr Tyr
            195             200             205

Asn Ser Ala Leu Lys Ser Arg Leu Thr Ile Ile Lys Asp Asn Ser Lys
            210             215             220

Ser Gln Val Phe Leu Lys Met Asn Ser Leu Gln Thr Asp Asp Thr Ala
225             230             235             240
```

-continued

```
Ile Tyr Tyr Cys Ala Lys His Tyr Tyr Gly Gly Ser Tyr Ala Met
            245                 250                 255

Asp Tyr Trp Gly Gln Gly Thr Thr Val Thr Val Ser Ser Tyr Val Thr
            260                 265                 270

Val Ser

<210> SEQ ID NO 3
<211> LENGTH: 227
<212> TYPE: PRT
<213> ORGANISM: Homo sapiens

<400> SEQUENCE: 3

Met Ala Val Arg Arg Asp Ser Val Trp Lys Tyr Cys Trp Gly Val Leu
1               5                   10                  15

Met Val Leu Cys Arg Thr Ala Ile Ser Lys Ser Ile Val Leu Glu Pro
            20                  25                  30

Ile Tyr Trp Asn Ser Ser Asn Ser Lys Phe Leu Pro Gly Gln Gly Leu
        35                  40                  45

Val Leu Tyr Pro Gln Ile Gly Asp Lys Leu Asp Ile Ile Cys Pro Lys
    50                  55                  60

Val Asp Ser Lys Thr Val Gly Gln Tyr Glu Tyr Tyr Lys Val Tyr Met
65                  70                  75                  80

Val Asp Lys Asp Gln Ala Asp Arg Cys Thr Ile Lys Lys Glu Asn Thr
                85                  90                  95

Pro Leu Leu Asn Cys Ala Lys Pro Asp Gln Asp Ile Lys Phe Thr Ile
            100                 105                 110

Lys Phe Gln Glu Phe Ser Pro Asn Leu Trp Gly Leu Glu Phe Gln Lys
        115                 120                 125

Asn Lys Asp Tyr Tyr Ile Ile Ser Thr Ser Asn Gly Ser Leu Glu Gly
    130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
                165                 170                 175

Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
        195                 200                 205

Asp Gly Asn Ser Ala Gly His Ser Gly Asn Asn Ile Leu Gly Ser Glu
    210                 215                 220

Val Ala Leu
225

<210> SEQ ID NO 4
<211> LENGTH: 14
<212> TYPE: PRT
<213> ORGANISM: Artificial Sequence
<220> FEATURE:
<223> OTHER INFORMATION: Linker

<400> SEQUENCE: 4

Glu Pro Lys Ser Cys Asp Lys Thr His Thr Cys Pro Pro Cys
1               5                   10

<210> SEQ ID NO 5
<211> LENGTH: 241
<212> TYPE: PRT
```

-continued

<213> ORGANISM: Artificial Sequence
<220> FEATURE:
<223> OTHER INFORMATION: Linker

<400> SEQUENCE: 5

```
Ser Gln Asp Pro Ala Glu Pro Lys Ser Pro Asp Lys Thr His Thr Cys
1               5                   10                  15

Pro Pro Cys Pro Ala Pro Glu Leu Leu Gly Gly Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110

Val Ser Asn Lys Ala Leu Pro Ala Pro Ile Glu Lys Thr Ile Ser Lys
            115                 120                 125

Ala Lys Gly Gln Pro Arg Glu Pro Gln Val Tyr Thr Leu Pro Pro Ser
    130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
                180                 185                 190

Ser Phe Phe Leu Tyr Ser Lys Leu Thr Val Asp Lys Ser Arg Trp Gln
            195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys Lys Asp Pro
225                 230                 235                 240

Lys
```

<210> SEQ ID NO 6
<211> LENGTH: 5
<212> TYPE: PRT
<213> ORGANISM: Artificial Sequence
<220> FEATURE:
<223> OTHER INFORMATION: Linker

<400> SEQUENCE: 6

```
Ser Ser Ala Ala Ala
1               5
```

<210> SEQ ID NO 7
<211> LENGTH: 68
<212> TYPE: PRT
<213> ORGANISM: Homo sapiens

<400> SEQUENCE: 7

```
Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30
```

-continued

```
Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65

<210> SEQ ID NO 8
<211> LENGTH: 107
<212> TYPE: PRT
<213> ORGANISM: Homo sapiens

<400> SEQUENCE: 8

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 9
<211> LENGTH: 112
<212> TYPE: PRT
<213> ORGANISM: Homo sapiens

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 695
<212> TYPE: PRT
<213> ORGANISM: Homo sapiens

<400> SEQUENCE: 10

Met Glu Leu Ala Ala Leu Cys Arg Trp Gly Leu Leu Leu Ala Leu Leu
1               5                   10                  15
```

-continued

```
Pro Pro Gly Ala Ala Ser Thr Gln Val Cys Thr Gly Thr Asp Met Lys
        20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
        130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
        210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
        290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
        370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
```

-continued

```
          435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
            645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
            675                 680                 685
Arg Leu Leu Gln Glu Thr Glu
    690                 695

<210> SEQ ID NO 11
<211> LENGTH: 580
<212> TYPE: PRT
<213> ORGANISM: Homo sapiens

<400> SEQUENCE: 11

Met Glu Leu Arg Val Leu Leu Cys Trp Ala Ser Leu Ala Ala Ala Leu
1                   5                   10                  15
Glu Glu Thr Leu Leu Asn Thr Lys Leu Glu Thr Ala Asp Leu Lys Trp
            20                  25                  30
Val Thr Phe Pro Gln Val Asp Gly Gln Trp Glu Glu Leu Ser Gly Leu
        35                  40                  45
Asp Glu Glu Gln His Ser Val Arg Thr Tyr Glu Val Cys Asp Val Gln
    50                  55                  60
Arg Ala Pro Gly Gln Ala His Trp Leu Arg Thr Gly Trp Val Pro Arg
65                  70                  75                  80
Arg Gly Ala Val His Val Tyr Ala Thr Leu Arg Phe Thr Met Leu Glu
                85                  90                  95
Cys Leu Ser Leu Pro Arg Ala Gly Arg Ser Cys Lys Glu Thr Phe Thr
            100                 105                 110
```

-continued

```
Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
            195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
            355                 360                 365

Ser Cys Ala Pro Cys Gly Gly Asp Leu Thr Phe Asp Pro Gly Pro Arg
    370                 375                 380

Asp Leu Val Glu Pro Trp Val Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Val
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
            515                 520                 525

Asp Glu Ser Glu Gly Trp Arg Glu Gln Leu Ala Leu Ile Ala Gly Thr
```

```
      530              535              540
Ala Val Val Gly Val Val Leu Val Leu Val Val Ile Val Val Ala Val
545              550              555              560

Leu Cys Leu Arg Lys Gln Ser Asn Gly Arg Glu Ala Glu Tyr Ser Asp
                565              570              575

Lys His Gly Gln
            580

<210> SEQ ID NO 12
<211> LENGTH: 288
<212> TYPE: PRT
<213> ORGANISM: Homo sapiens

<400> SEQUENCE: 12

Met Gly His Thr Arg Arg Gln Gly Thr Ser Pro Ser Lys Cys Pro Tyr
1               5                  10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
                260                 265                 270

Glu Arg Arg Arg Asn Glu Arg Leu Arg Arg Glu Ser Val Arg Pro Val
            275                 280                 285

<210> SEQ ID NO 13
<211> LENGTH: 254
<212> TYPE: PRT
<213> ORGANISM: Homo sapiens
```

-continued

<400> SEQUENCE: 13

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Leu Ala Ala Ala Cys Ala Val Phe
                35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
                115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
                195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

<210> SEQ ID NO 14
<211> LENGTH: 277
<212> TYPE: PRT
<213> ORGANISM: Homo sapiens

<400> SEQUENCE: 14

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
                35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
                100                 105                 110
```

-continued

```
Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
            275

<210> SEQ ID NO 15
<211> LENGTH: 183
<212> TYPE: PRT
<213> ORGANISM: Homo sapiens

<400> SEQUENCE: 15

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
                100                 105                 110

Val Asn Ile Ser Leu His Tyr Gln Lys Asp Glu Glu Pro Leu Phe Gln
            115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 16
```

-continued

```
<211> LENGTH: 334
<212> TYPE: PRT
<213> ORGANISM: Homo sapiens

<400> SEQUENCE: 16

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
            165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
    195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
            245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Ser
            325                 330
```